United States Patent
Eki

(10) Patent No.: US 11,820,289 B2
(45) Date of Patent: Nov. 21, 2023

(54) SOLID-STATE IMAGING DEVICE AND ELECTRONIC DEVICE

(71) Applicant: Sony Semiconductor Solutions Corporation, Kanagawa (JP)

(72) Inventor: Ryoji Eki, Kanagawa (JP)

(73) Assignee: Sony Semiconductor Solutions Corporation, Kanagawa (JP)

(*) Notice: Subject to any disclaimer, the term of this patent is extended or adjusted under 35 U.S.C. 154(b) by 70 days.

(21) Appl. No.: 17/251,953

(22) PCT Filed: Jul. 29, 2019

(86) PCT No.: PCT/JP2019/029715
§ 371 (c)(1),
(2) Date: Dec. 14, 2020

(87) PCT Pub. No.: WO2020/027074
PCT Pub. Date: Feb. 6, 2020

(65) Prior Publication Data
US 2021/0264192 A1 Aug. 26, 2021

(30) Foreign Application Priority Data

Jul. 31, 2018 (JP) ................................ 2018-144173
Jul. 29, 2019 (JP) ................................ 2019-139196

(51) Int. Cl.
*B60R 1/00* (2022.01)
*G06N 3/08* (2023.01)
(Continued)

(52) U.S. Cl.
CPC ............... *B60R 1/00* (2013.01); *G06F 18/213* (2023.01); *G06N 3/08* (2013.01); *G06V 10/10* (2022.01);
(Continued)

(58) Field of Classification Search
CPC ............ H04N 5/23218; H04N 5/2252; H04N 5/23206; H04N 5/335; H04N 5/341;
(Continued)

(56) References Cited

U.S. PATENT DOCUMENTS 8,417,046 B1* 4/2013 McDougal ............. G06V 10/20
382/254
8,610,787 B2* 12/2013 Namba ............... H04N 5/23219
348/222.1
(Continued)

FOREIGN PATENT DOCUMENTS

EP        2372308 A2    10/2011
JP     2017-158065 A     9/2019
(Continued)

OTHER PUBLICATIONS

International Search Report, International Application No. PCT/JP2019/029715, dated Sep. 27, 2019.
(Continued)

*Primary Examiner* — Michael S Osinski
(74) *Attorney, Agent, or Firm* — Michael Best & Friedrich LLP

(57) ABSTRACT

A solid-state imaging device includes: an imager (11) configured to acquire image data; a processing unit (14) configured to execute, on the image data or data based on the image data, processing of extracting a specific region based on a neural network calculation model; and an output unit (16) configured to output image data fabricated based on the specific region or the image data read from the imager based on the specific region.

17 Claims, 15 Drawing Sheets

(51) Int. Cl.

| | |
|---|---|
| G06F 18/213 | (2023.01) |
| H04N 23/61 | (2023.01) |
| H04N 23/51 | (2023.01) |
| H04N 23/661 | (2023.01) |
| H04N 25/40 | (2023.01) |
| G06V 10/25 | (2022.01) |
| G06V 10/12 | (2022.01) |
| G06V 10/10 | (2022.01) |
| G06V 10/82 | (2022.01) |
| G06V 10/22 | (2022.01) |
| G06V 20/69 | (2022.01) |
| G06V 10/94 | (2022.01) |
| G06V 20/56 | (2022.01) |
| G06V 40/16 | (2022.01) |
| G06V 10/46 | (2022.01) |
| H04N 23/50 | (2023.01) |
| H04N 25/00 | (2023.01) |
| G06V 20/58 | (2022.01) |

(52) U.S. Cl.
CPC .............. *G06V 10/12* (2022.01); *G06V 10/22* (2022.01); *G06V 10/25* (2022.01); *G06V 10/462* (2022.01); *G06V 10/82* (2022.01); *G06V 10/955* (2022.01); *G06V 20/56* (2022.01); *G06V 20/693* (2022.01); *G06V 40/166* (2022.01); *H04N 23/51* (2023.01); *H04N 23/61* (2023.01); *H04N 23/661* (2023.01); *H04N 25/40* (2023.01); *G06V 20/58* (2022.01); *H04N 23/555* (2023.01); *H04N 25/00* (2023.01)

(58) Field of Classification Search
CPC ....... H04N 2005/2255; H04N 5/23203; H04N 5/23219; H04N 5/23225; H04N 5/23229; H04N 13/239; H04N 9/64; H04N 5/232; H04N 5/232411; H04N 5/3454; H04N 5/374; H04N 5/378; H04N 5/379; H04N 9/04557; H04N 5/23245; H04N 5/2351; H04N 5/345; H04N 5/3559; H04N 5/3694; G06K 9/6232; G06N 3/08; G06V 10/462; G06V 10/10; G06V 10/12; G06V 10/25; G06V 20/58; G06V 10/22; G06V 10/82; G06V 10/955; G06V 20/56; G06V 20/693; G06V 40/166; A61B 1/043; A61B 1/045; A61B 1/0638; B60R 2300/30; B60R 1/00

See application file for complete search history.

(56) References Cited

U.S. PATENT DOCUMENTS

| | | | |
|---|---|---|---|
| 9,883,112 B1* | 1/2018 | Igor' Valer'Evich | H04N 5/23245 |
| 10,977,801 B2* | 4/2021 | Heo | G06V 10/143 |
| 11,430,259 B2* | 8/2022 | Chen | G06V 40/161 |
| 2010/0067749 A1* | 3/2010 | Kusama | H04N 23/611 382/118 |
| 2010/0182447 A1* | 7/2010 | Namba | G03B 13/36 348/222.1 |
| 2011/0262039 A1* | 10/2011 | Du | G06T 5/008 382/167 |
| 2015/0085170 A1 | 3/2015 | Takeda | |
| 2015/0229818 A1* | 8/2015 | Fukuyama | H04N 5/2354 348/367 |
| 2015/0256443 A1* | 9/2015 | Ozawa | H04L 45/121 370/329 |
| 2015/0334267 A1* | 11/2015 | Hirakawa | H04N 1/62 348/242 |
| 2015/0339838 A1* | 11/2015 | Friedman | G06T 11/60 345/641 |
| 2016/0005152 A1* | 1/2016 | Yang | G06V 10/30 382/275 |
| 2016/0012615 A1* | 1/2016 | Gao | G06T 11/005 382/131 |
| 2016/0259980 A1* | 9/2016 | Mlybari | G06T 7/277 |
| 2016/0328872 A1* | 11/2016 | Hauswiesner | G06T 11/60 |
| 2017/0169553 A1* | 6/2017 | Manhart | G06T 7/254 |
| 2017/0192666 A1* | 7/2017 | McCarthy | H04N 5/23216 |
| 2017/0262962 A1* | 9/2017 | Rad | G06T 5/007 |
| 2017/0267178 A1 | 9/2017 | Shiga et al. | |
| 2017/0339431 A1* | 11/2017 | Zhang | H04N 19/117 |
| 2018/0075290 A1* | 3/2018 | Chen | G06V 10/764 |
| 2018/0114073 A1* | 4/2018 | Zhang | G06V 20/53 |
| 2018/0268571 A1* | 9/2018 | Park | G06T 7/194 |
| 2018/0286037 A1* | 10/2018 | Zaharchuk | G06T 5/50 |
| 2018/0357800 A1* | 12/2018 | Oxholm | G06T 11/001 |
| 2019/0197353 A1* | 6/2019 | Yonetsuji | G06V 10/7788 |
| 2019/0279074 A1* | 9/2019 | Lin | G06V 10/764 |
| 2019/0294961 A1* | 9/2019 | Zuev | G06N 3/0454 |
| 2019/0311202 A1* | 10/2019 | Lee | G06T 9/002 |
| 2019/0377967 A1* | 12/2019 | Yabuuchi | G06V 40/173 |
| 2020/0163643 A1* | 5/2020 | Desaute | A61B 6/4233 |
| 2020/0279354 A1* | 9/2020 | Klaiman | G06N 3/04 |
| 2020/0286213 A1* | 9/2020 | Unger | H04N 1/4072 |
| 2020/0380683 A1* | 12/2020 | Tanaka | G06T 7/254 |
| 2020/0413012 A1* | 12/2020 | Alleysson | H04N 9/0455 |
| 2021/0018751 A1* | 1/2021 | Shmunk | G02B 27/0189 |
| 2021/0142095 A1* | 5/2021 | Shi | G06T 7/11 |
| 2021/0224567 A1* | 7/2021 | Wang | G06V 20/52 |
| 2021/0232806 A1* | 7/2021 | He | G06V 10/764 |
| 2021/0264192 A1* | 8/2021 | Eki | H04N 5/335 |
| 2021/0334942 A1* | 10/2021 | Wang | G06T 5/005 |

FOREIGN PATENT DOCUMENTS

| | | |
|---|---|---|
| WO | 2009/001530 A1 | 12/2008 |
| WO | 2017/187811 A1 | 11/2017 |
| WO | 2018/051809 A1 | 3/2018 |

OTHER PUBLICATIONS

Notification of Transmittal of the International Search Report and the Written Opinion of the International Searching Authority, or the Declaration (PCT/ISA/220), International Application No. PCT/JP2019/029715, dated Oct. 8, 2019.

K. Bong et al., "A 0.62mW ultra-low-power convolutional-neural-network face-recognition processor and a CIS integrated with always-on haar-like face detector," 2017 IEEE International Solid-State Circuits Conference (ISSCC), Date of Conference: Feb. 5-9, 2017.

Extended European Search Report dated Jul. 15, 2021 for corresponding European Application No. 19843827.7.

Japanese Office Action dated Apr. 27, 2021 for corresponding Japanese Application No. 2020-109273.

* cited by examiner

SOLID-STATE IMAGING DEVICE AND ELECTRONIC DEVICE

FIELD

The present disclosure relates to a solid-state imaging device and an electronic device. Specifically, the present disclosure relates to image data fabrication processing in a chip.

BACKGROUND

An image sensor including a complementary metal oxide semiconductor (CMOS) and a digital signal processor (DSP) is mounted on an instrument such as a digital camera. In the image sensor, a captured image is supplied to the DSP, provided with various processing at the DSP, and output to an external device such as an application processor.

CITATION LIST

Patent Literature

Patent Literature 1: WO 2018/051809

SUMMARY

Technical Problem

However, in the above-described conventional technology, it is typical that uncomplicated image processing such as noise removal is executed at the DSP in the image sensor whereas complicated processing such as face authentication using image data is executed at, for example, an application processor. Accordingly, an image captured by the image sensor is directly output to the application processor, and thus it is desired to execute fabrication processing in a chip of the image sensor in terms of security and privacy.

Thus, the present disclosure provides a solid-state imaging device and an electronic device that are capable of executing fabrication processing in a chip of an image sensor.

Solution to Problem

To solve the above-described problem, a solid-state imaging device according to the present disclosure includes an imager configured to acquire image data, a processing unit configured to execute, on the image data or data based on the image data, processing of extracting a specific region based on a neural network calculation model, and an output unit configured to output image data fabricated based on the specific region or the image data read from the imager based on the specific region.

Since the processing unit configured to extract a specific region as a fabrication target from image data acquired by the imager is mounted on the solid-state imaging device, extraction and fabrication processing of a fabrication region can be executed in a chip. Accordingly, it is possible to prevent privacy information or the like included in the unprocessed image data from being output to the outside of the chip, thereby achieving a secure solid-state imaging device. In addition, it is possible to obtain an advantage of reducing the amount of data output from the solid-state imaging device to the outside.

Advantageous Effects of Invention

According to the present disclosure, it is possible to execute fabrication processing in a chip of an image sensor.

Note that the above-described effect is not necessarily restrictive, but any effect indicated in the present disclosure may be achieved.

DESCRIPTION OF EMBODIMENTS

Figure 1:
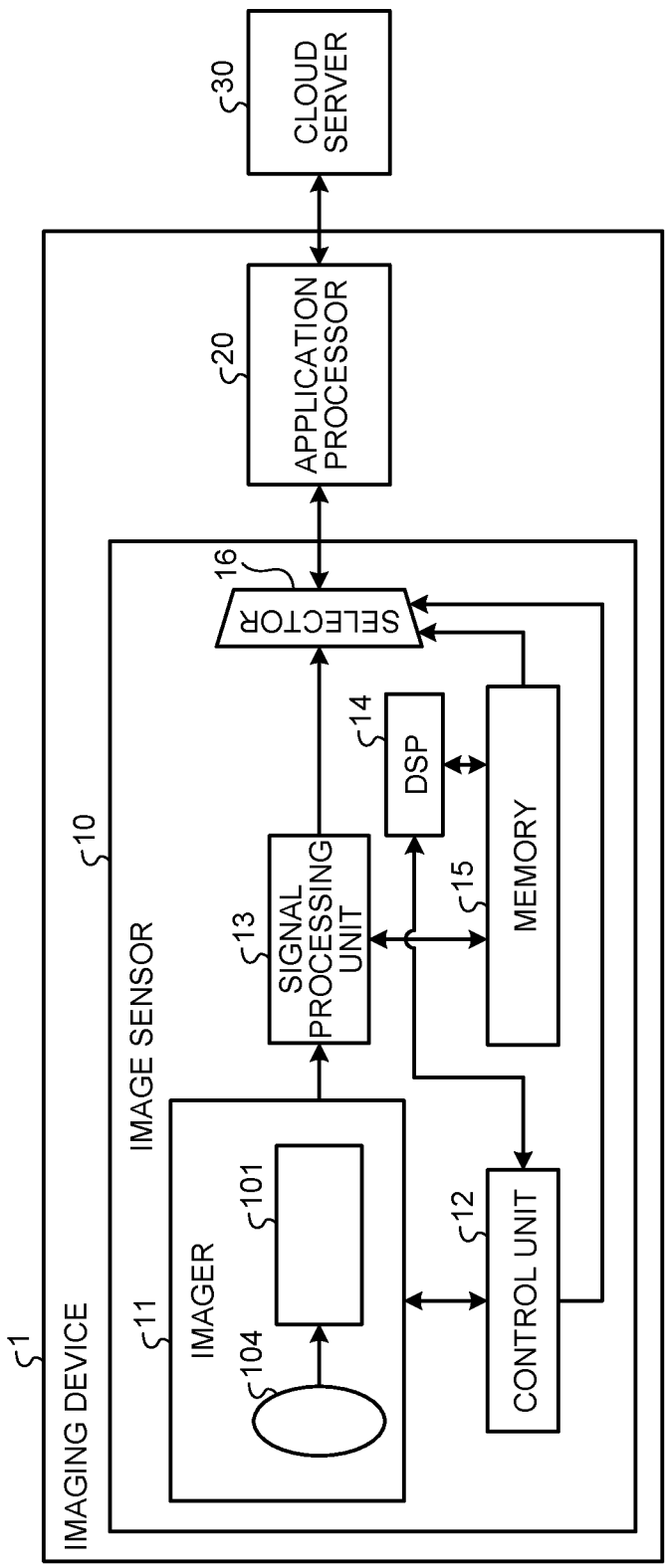
FIG. 1 is a block diagram illustrating an exemplary schematic configuration of an imaging device as an electronic device according to a first embodiment.

Embodiments of the present disclosure will be described below in detail with reference to the accompanying drawings. Note that, in the embodiments below, any identical sites are denoted by an identical reference sign, and duplicate description thereof is omitted.

The present disclosure will be described in accordance with the order of contents described below.

1. First Embodiment
2. Modification of first embodiment
3. Second Embodiment
4. Third Embodiment
5. Chip configuration of image sensor
6. Exemplary arrangement
7. Other embodiments
8. Exemplary application to moving object
9. Exemplary application to endoscope operation system
10. Exemplary application to whole slide imaging (WSI) system

1. First Embodiment 1-1. Configuration of Image Processing System According to First Embodiment FIG. 1 is a block diagram illustrating an exemplary schematic configuration of an imaging device as an electronic device according to a first embodiment. As illustrated in FIG. 1, this imaging device 1 is connected with a cloud server 30 to perform communication therebetween. Note that the imaging device 1 and the cloud server 30 are connected with each other through various wired and wireless networks, a universal serial bus (USB) cable, and the like to perform communication therebetween.

The cloud server 30 is an exemplary server device configured to store image data such as still and moving images transmitted from the imaging device 1. For example, the cloud server 30 stores the image data in arbitrary units of user, date, image capturing place, and the like and can provide various services such as album production using the image data.

The imaging device 1 is an exemplary electronic device including an image sensor 10 and an application processor 20, and is, for example, a digital camera, a digital video camera, a tablet terminal, or a smartphone. Note that embodiments below are described by using an example in which an image is captured, but the present disclosure is not limited thereto, and a moving image or the like can be processed in a similar manner.

The image sensor 10 is, for example, a complementary metal oxide semiconductor (CMOS) image sensor constituted by one chip, receives incident light, performs photoelectric conversion, and outputs image data corresponding to the received-light quantity of the incident light to the application processor 20.

The application processor 20 is an exemplary processor such as a central processing unit (CPU) configured to execute various applications. The application processor 20 executes various kinds of processing corresponding to an application, such as display processing of displaying the image data input from the image sensor 10 on a display, biometric authentication processing using the image data, and transmission processing of transmitting the image data to the cloud server 30.

1-2. Configuration of Imaging Device According to First Embodiment

As illustrated in FIG. 1, the imaging device 1 includes the image sensor 10 as a solid-state imaging device, and the application processor 20. The image sensor includes an imager 11, a control unit 12, a signal processing unit 13, a DSP (also referred to as processing unit) 14, a memory 15, and a selector 16 (also referred to as output unit).

The imager 11 includes an optical system 104 including a zoom lens, a focus lens, an aperture, and the like, and a pixel array unit 101 having a configuration in which unit pixels each including a light receiving element such as a photodiode are arrayed in a two-dimensional matrix. Light incident from the outside is imaged, through the optical system 104, onto a light-receiving surface of the pixel array unit 101, on which the light receiving elements are arrayed. Each unit pixel of the pixel array unit 101 photoelectrically converts light incident on the light receiving element and accumulates electric charge in accordance with the light quantity of the incident light in a readable manner.

The imager 11 also includes a converter (analog-to-digital converter; hereinafter referred to as ADC) 17 (refer to FIG. 2, for example). The ADC 17 generates digital image data by converting an analog pixel signal read from the imager 11 for each unit pixel into a digital value, and outputs the generated image data to the signal processing unit 13. Note that the ADC 17 may include, for example, a voltage generation circuit configured to generate drive voltage for driving the imager 11 from power voltage or the like.

The size of image data output from the imager 11 may be selected from among a plurality of sizes such as 12 M (3968×2976) pixels and a Video Graphics Array (VGA) size (640×480 pixels Z). In addition, for example, it is possible to select whether a color image of RGB (red, green, and blue) or a grayscale image with luminance only is to be generated from the image data output from the imager 11. Each selection may be performed as a kind of setting of an image capturing mode.

The control unit 12 controls each component in the image sensor 10 in accordance with, for example, a user operation and a set operation mode.

The signal processing unit 13 executes various kinds of signal processing on digital image data read from the imager 11 or digital image data read from the memory 15 (hereinafter referred to as processing target image data). For example, when the processing target image data is a color image, the signal processing unit 13 performs format conversion of the image data into YUV image data, RGB image data, or the like. The signal processing unit 13 also executes processing such as noise removal or white balance adjustment on the processing target image data as necessary. In addition, the signal processing unit 13 executes, on the processing target image data, various kinds of signal processing (also referred to as preprocessing) needed for the DSP 14 to process the image data.

The DSP 14 executes, for example, a computer program stored in the memory 15 to function as a processing unit configured to execute various kinds of processing by using a learning-completed model produced by machine learning using a deep neural network (DNN). For example, the DSP 14 executes arithmetic processing based on a learning-completed model stored in the memory 15 to execute processing of multiplying image data by a dictionary coefficient stored in the memory 15. A result (calculation result) obtained through such arithmetic processing is output to the memory 15 and/or the selector 16. Note that the calculation result may include image data obtained by executing arithmetic processing using a learning-completed model, and various kinds of information (metadata) obtained from the image data. In addition, a memory controller configured to control access to the memory 15 may be incorporated in the DSP 14.

Some types of arithmetic processing use, for example, a learning-completed learning model as an exemplary neural network calculation model. For example, the DSP 14 can execute DSP processing as various kinds of processing by using the learning-completed learning model. For example, the DSP 14 reads image data from the memory 15, inputs the image data into the learning-completed learning model, and acquires, as a result output from the learning-completed model, a face position such as a face outline or a region of a face image. Then, the DSP 14 generates fabricated image data by executing processing such as masking, mosaicing, or avatar creation on an extracted face position in the image data. Thereafter, the DSP 14 stores the generated fabricated image data in the memory 15.

The learning-completed learning model includes a DNN, a support vector machine, or the like having learned, for example, detection of the face position of a person by using learning data. Having received image data as determination target data, the learning-completed learning model outputs region information such as an address that specifies a determination result, in other words, a face position. Note that the DSP 14 may update a learning model by changing weights of various parameters in the learning model by using learning data, may prepare a plurality of learning models and change a learning model to be used in accordance with the contents of arithmetic processing, or may acquire or update a learning-completed learning model from an external device, thereby executing the above-described arithmetic processing.

Note that image data as a processing target of the DSP 14 may be image data normally read from the pixel array unit 101 or may be image data having a data size reduced by thinning pixels of the normally read image data. Alternatively, the image data may be image data read in a data size smaller than normal by executing thinned-pixel reading from the pixel array unit 101. Note that the normal reading may be reading without pixel thinning.

Through such face position extraction and fabrication processing by using a learning model, it is possible to generate fabricated image data provided with masking at a face position of image data, fabricated image data provided with mosaic processing at a face position of image data, or fabricated image data provided with avatar creation by placing a character at a face position of image data.

The memory 15 stores image data output from the imager 11, image data provided with signal processing by the signal processing unit 13, the calculation result obtained at the DSP 14, and the like as necessary. The memory 15 also stores, as a computer program and a dictionary coefficient, an algorithm of a learning-completed learning model, which is executed by the DSP 14.

In addition to image data output from the signal processing unit 13 and image data (hereinafter referred to as fabricated image data) provided with arithmetic processing and output from the DSP 14, the memory 15 may store an ISO (International Organization for Standardization) sensitivity, an exposure time, a frame rate, a focus, an image capturing mode, a clipping range, and the like. Thus, the memory 15 may store various kinds of image capturing information set by a user.

The selector 16 selectively outputs fabricated image data output from the DSP 14 or image data stored in the memory 15 in accordance with, for example, a selection control signal from the control unit 12. For example, the selector 16 selects, based on setting by the user or the like, any of calculation results such as fabricated image data and metadata stored in the memory 15, and outputs the selected calculation result to the application processor 20.

For example, when a fabrication processing mode in which fabricated image data is output is selected, the selector 16 reads fabricated image data generated by the DSP 14 from the memory 15 and outputs the fabricated image data to the application processor. When a normal processing mode in which fabricated image data is not output is selected, the selector 16 outputs, to the application processor, image data input from the signal processing unit 13. Note that, when a first processing mode is selected, the selector 16 may directly output, to the application processor 20, a calculation result output from the DSP 14.

The image data and the fabricated image data output from the selector 16 as described above are input to the application processor 20 configured to process display, a user interface, and the like. The application processor is achieved by, for example, a CPU or the like and executes an operating system, various kinds of application software, and the like. The application processor 20 may have functions of a graphics processing unit (GPU), a baseband processor, and the like. The application processor 20 executes various kinds of processing on input image data and calculation result as needed, executes display to the user, and executes transmission to the external cloud server 30 through a predetermined network 40.

Note that various kinds of networks such as the Internet, a wired local area network (LAN), a wireless LAN, a mobile communication network, and Bluetooth (registered trademark) may be applied as the predetermined network 40. The transmission destination of image data and a calculation result is not limited to the cloud server 30 but may be various kinds of information processing devices (systems) having a communication function, for example, a stand-alone server, a file server configured to store various kinds of data, and a communication terminal such as a cellular phone.

1-3. Description of Image Fabrication According to First Embodiment

Figure 2:
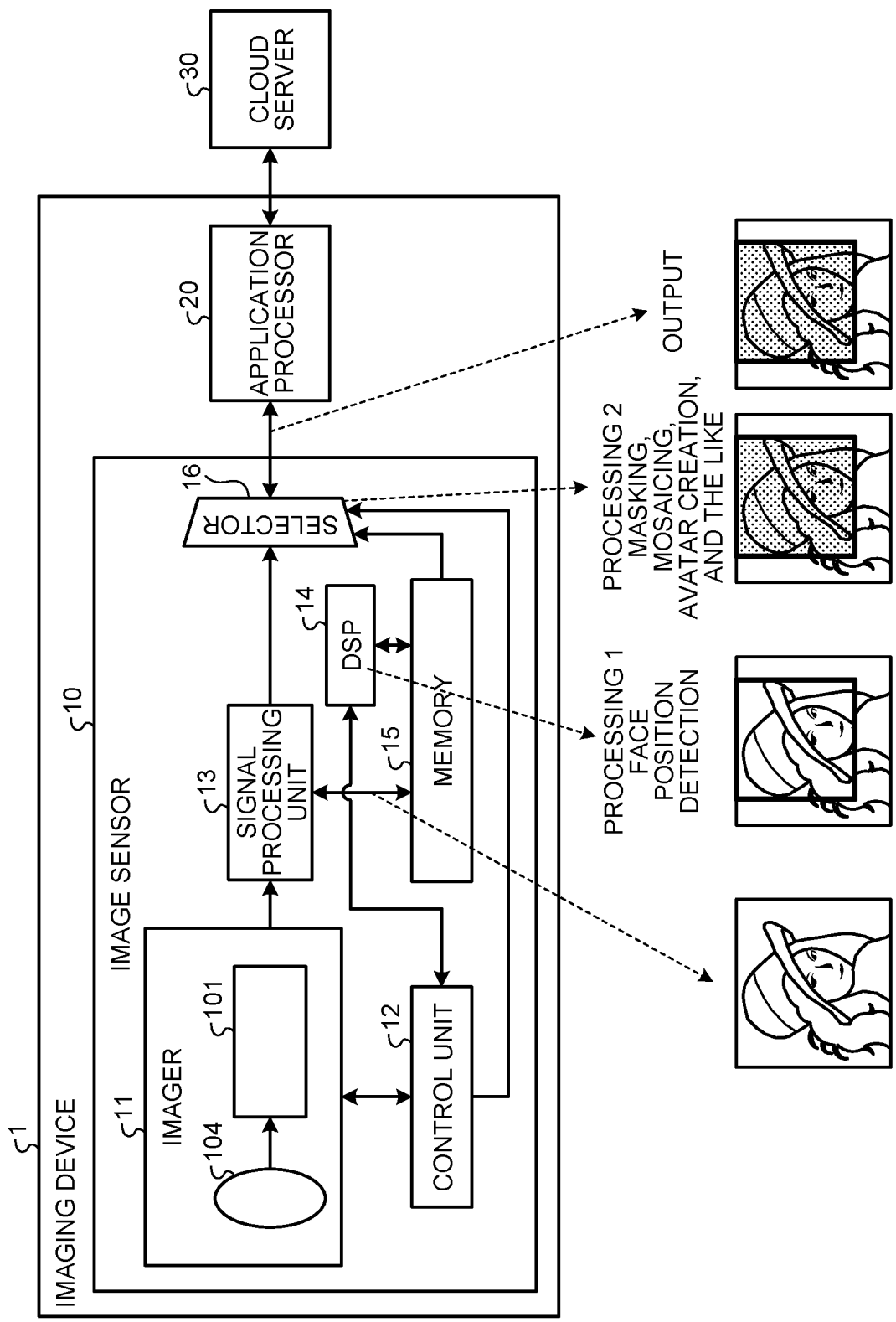
FIG. 2 is a diagram for description of image fabrication according to the first embodiment.

FIG. 2 is a diagram for description of image fabrication according to the first embodiment. As illustrated in FIG. 2, the signal processing unit 13 performs signal processing on image data read from the imager 11 and stores the image data in the memory 15. The DSP 14 reads the image data from the memory 15 and detects a face position from the image data by executing face detection using a learning-completed learning model (Processing 1).

Subsequently, the DSP 14 generates fabricated image data by executing the fabrication processing (Processing 2) of providing masking, mosaicing, and the like on the detected face position and stores the fabricated image data in the memory 15. Thereafter, the selector 16 outputs the fabricated image data in which a face region is fabricated in accordance with selection by the user to the application processor 20.

1-4. Process of Processing According to First Embodiment

Figure 3:
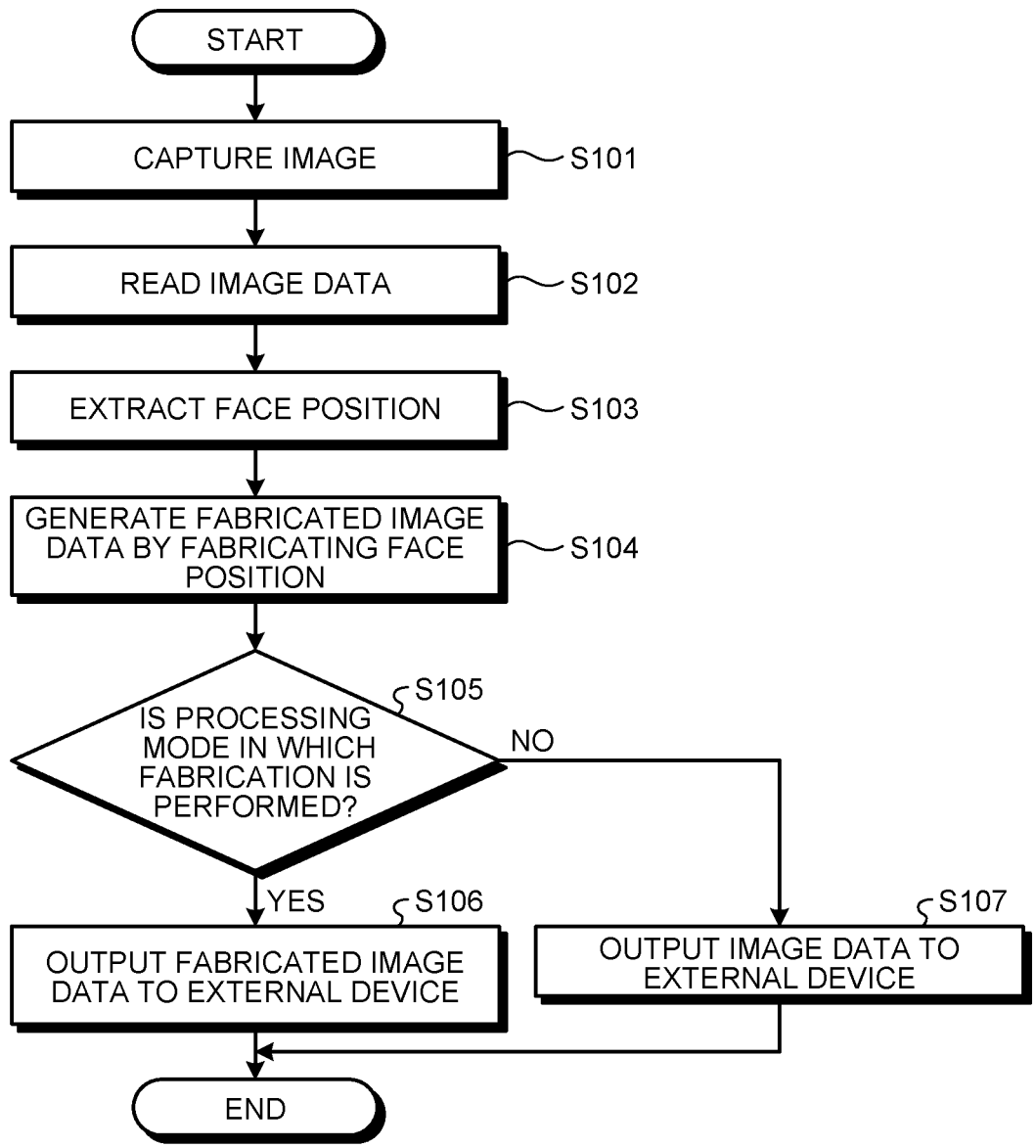
FIG. 3 is a flowchart illustrating the process of fabrication processing according to the first embodiment.

FIG. 3 is a flowchart illustrating the process of the fabrication processing according to the first embodiment. As illustrated in FIG. 3, image data captured by the imager 11 is stored in the memory 15 (S101).

Then, the DSP 14 reads the image data from the memory 15 (S102) and detects a face position by using a learning-completed learning model (S103). Subsequently, the DSP 14 generates fabricated image data by fabricating the image data at the face position and stores the fabricated image data in the memory 15 (S104).

Thereafter, when the fabrication processing mode as a processing mode in which fabrication is performed is selected (Yes at S105), the selector 16 reads the fabricated image data from the memory 15 and outputs the fabricated image data to an external device such as the application processor 20 (S106).

When the normal processing mode as a processing mode in which no fabrication is performed is selected (No at S105), the selector 16 reads the image data not provided with the fabrication processing from the memory 15 and outputs the image data to an external device such as the application processor 20 (S107).

1-5. Effects

As described above, the image sensor 10 can execute the fabrication processing in a closed region in one chip when fabrication is necessary, it is possible to prevent captured image data from being directly output to the outside, thereby achieving security improvement and privacy protection. In addition, the image sensor 10 allows the user to select whether to execute fabrication, and thus a processing mode can be selected in accordance with usage to improve convenience of the user.

2. Modification of the First Embodiment

The first embodiment describes above an example in which masking and the like are executed at a face position, but the fabrication processing is not limited thereto. For example, a partial image to which a face position is extracted may be generated.

Figure 4:
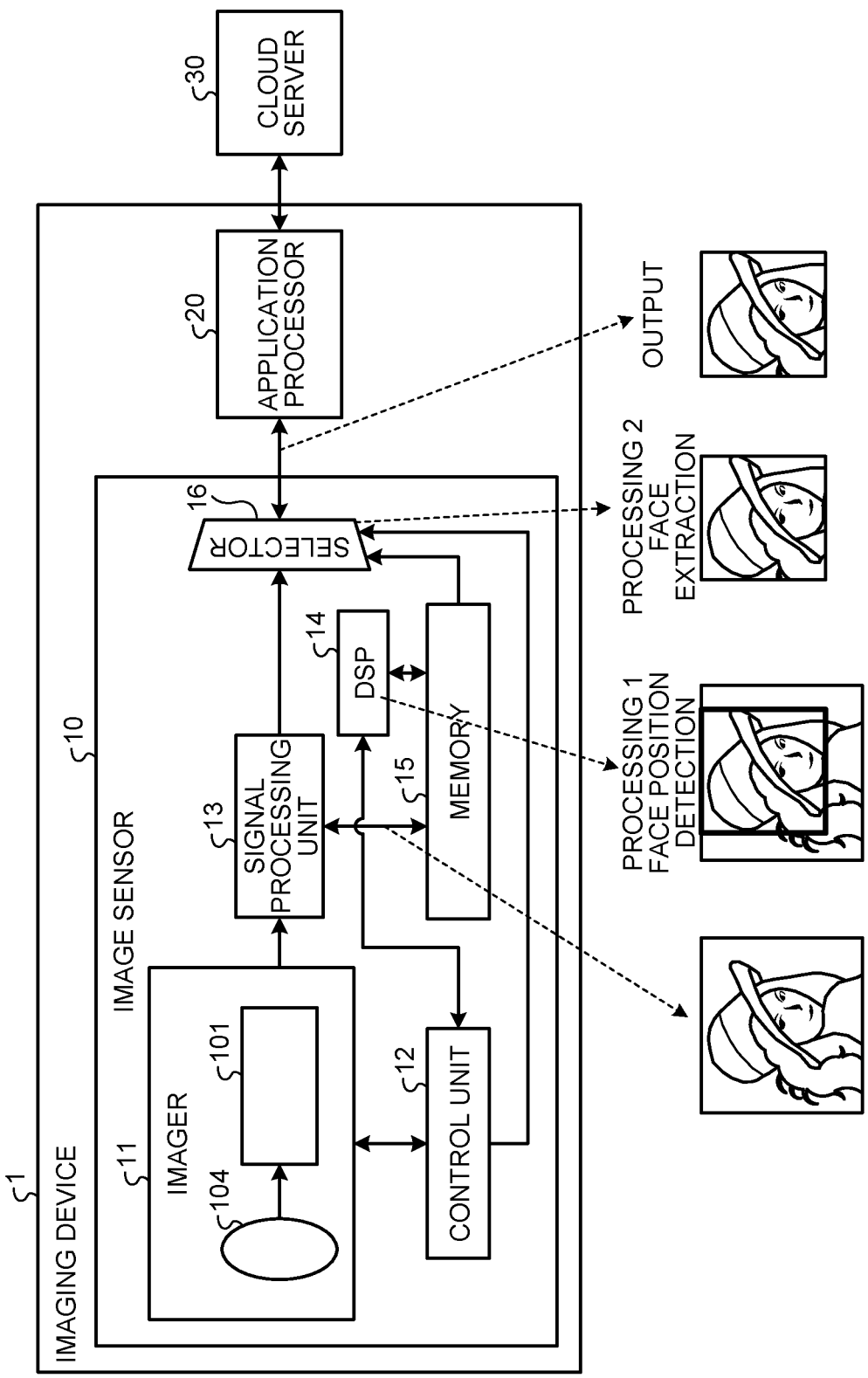
FIG. 4 is a diagram for description of a modification of the first embodiment.

FIG. 4 is a diagram for description of a modification of the first embodiment. As illustrated in FIG. 4, the signal processing unit 13 performs signal processing on image data read from the imager 11 and stores the image data in the memory 15. The DSP 14 reads the image data from the memory 15 and detects a face position from the image data by executing face detection using a learning-completed learning model (Processing 1).

Subsequently, the DSP 14 generates a partial image data to which the detected face position is extracted (Processing 2), and stores the partial image data in the memory 15. Thereafter, the selector 16 outputs partial image data of the face in accordance with selection of the user to the application processor 20.

As described above, the image sensor 10 can execute extraction of partial image data in a closed region in one chip when fabrication is necessary, and thus can output an image in accordance with processing of the application processor 20, such as person specification, face authentication, or image collection for each person. As a result, it is possible to prevent transmission of an unnecessary image, thereby achieving security improvement and privacy protection as well as data volume reduction.

3. Second Embodiment

3-1. Description of Imaging Device According to Second Embodiment

Although the first embodiment describes an example in which the DSP 14 executes the fabrication processing, the present disclosure is not limited thereto, and the selector 16 may perform the fabrication processing. Thus, a second embodiment describes an example in which the selector 16 performs the fabrication processing.

Figure 5:
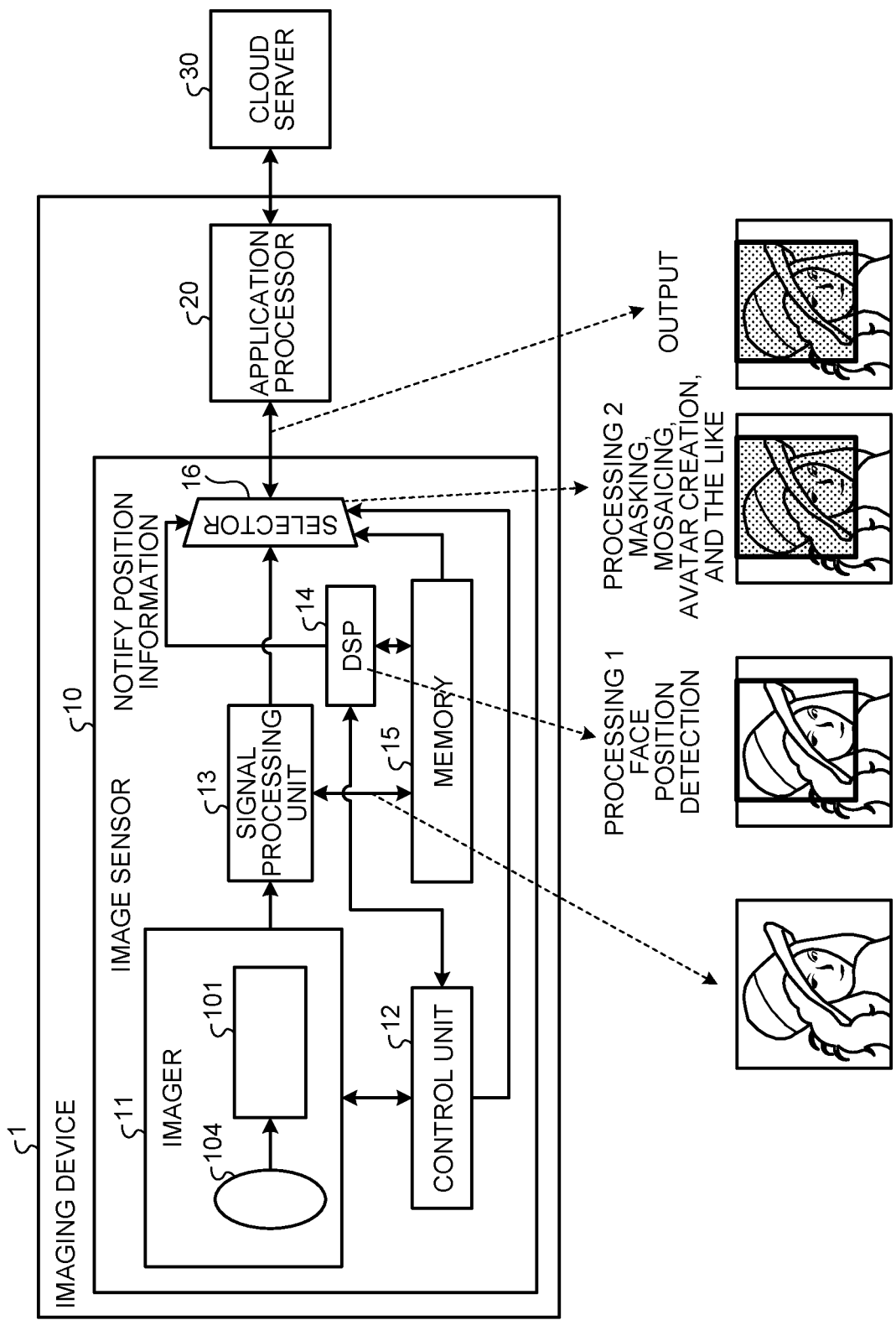
FIG. 5 is a diagram for description of the imaging device according to a second embodiment.

FIG. 5 is a diagram for description of an imaging device according to the second embodiment. As illustrated in FIG. 5, the configuration of the image sensor 10 according to the second embodiment is same as that of the image sensor 10 according to the first embodiment, and thus detailed description thereof is omitted. Difference from the first embodiment is that the DSP 14 of the image sensor notifies the selector 16 of position information of a face position extracted by using a learning model.

For example, as illustrated in FIG. 5, the signal processing unit 13 performs signal processing on image data read from the imager 11 and stores the image data in the memory 15. The DSP 14 reads the image data from the memory and detects a face position from the image data by executing face detection using a learning-completed learning model (Processing 1). Then, the DSP 14 notifies the selector 16 of position information such as an address that specifies the face position.

When the fabrication processing is selected by the user, the selector 16 reads image data from the memory and specifies a region of interest (ROI) as a fabrication target by using the position information acquired from the DSP 14. Then, the selector 16 generates fabricated image data by executing the fabrication processing such as masking on the specified ROI (Processing 2) and outputs the fabricated image data to the application processor 20. Note that the selector 16 stores the fabricated image data in the memory 15.

3-2. First Modification of Second Embodiment

Similarly to the above-described modification of the first embodiment, in the second embodiment as well, the selector 16 may generate a partial image to which a face position is extracted.

Figure 6:
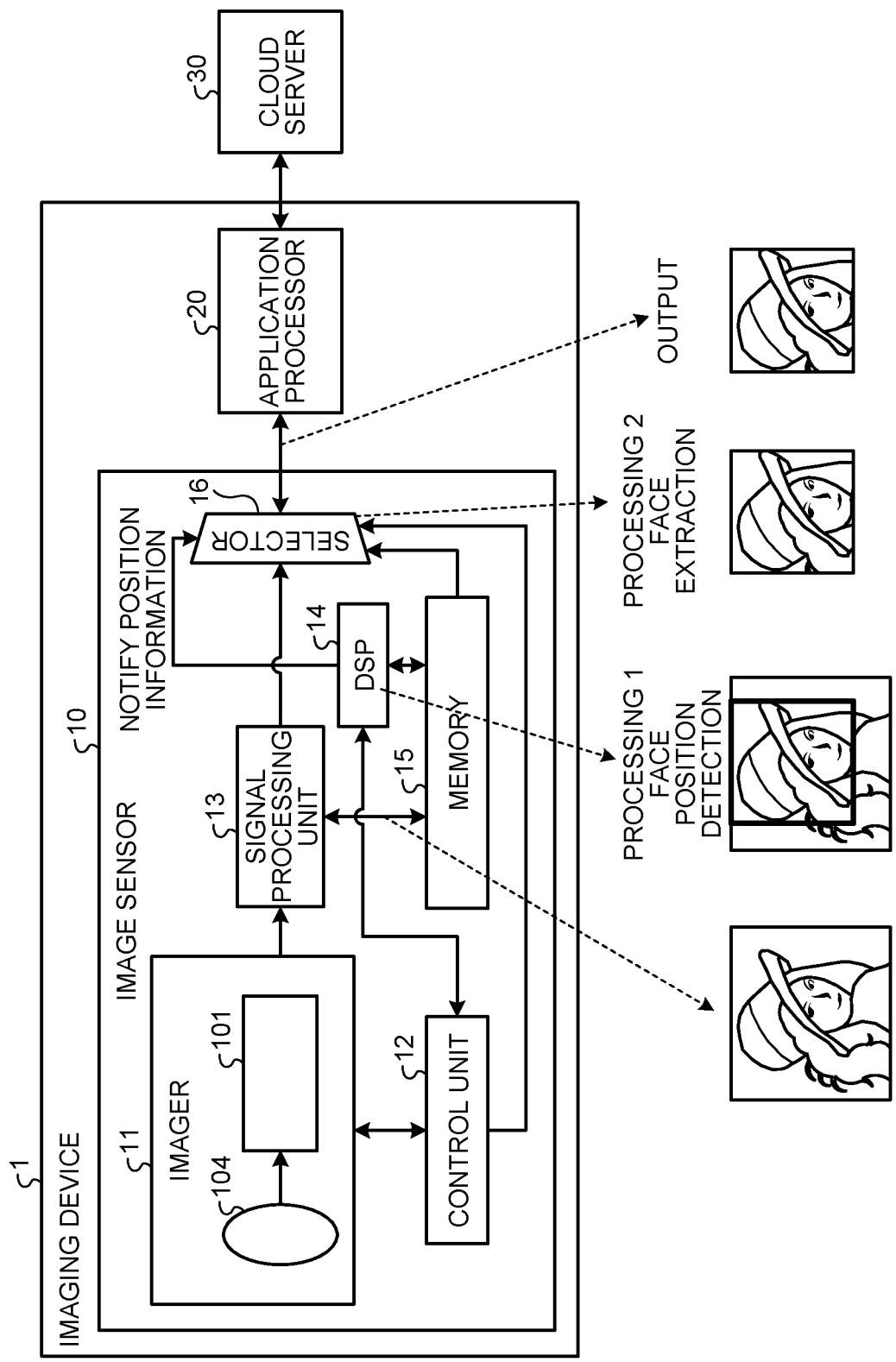
FIG. 6 is a diagram for description of a modification of the second embodiment.

FIG. 6 is a diagram for description of a first modification of the second embodiment. As illustrated in FIG. 6, the signal processing unit 13 performs signal processing on image data read from the imager 11 and stores the image data in the memory 15. The DSP 14 reads the image data from the memory 15 and detects a face position from the image data by executing face detection using a learning-completed learning model (Processing 1). Then, the DSP 14 notifies the selector 16 of position information such as an address that specifies the face position.

Subsequently, when the fabrication processing is selected by the user, the selector 16 reads the image data from the memory 15 and specifies a region of interest (ROI) as a fabrication target by using the position information acquired from the DSP 14. Thereafter, the selector 16 generates partial image data to which a part corresponding to the ROI is extracted from the image data (Processing 2), and outputs the partial image data to the application processor 20.

3-3. Second Modification of Second Embodiment

Although the second embodiment and the first modification thereof describe above an example case in which the selector 16 performs Processing 2 such as ROI extraction (also referred to as clipping or trimming) and fabrication (for example, masking) on image data stored in the memory 15, the present disclosure is not limited thereto, and for example, the selector 16 may directly execute Processing 2 such as ROI clipping and fabrication (for example, masking) on image data output from the signal processing unit 13.

3-4. Third Modification of Second Embodiment

Image data read from the imager 11 may be partial image data of an ROI only or image data including no ROI. In this case, the control unit 12 is notified of a face position extracted from a first frame by the DSP 14 and executes, for the imager 11, reading of partial image data from a pixel region corresponding to an ROI in a second frame as the next frame of the first frame, and reading of image data from a pixel region corresponding to a region other than the ROI.

Note that in the second embodiment and the modification thereof, the selector 16 is not limited to the fabrication processing such as masking but may rewrite a region corresponding to an ROI in image data into another image and output the image or may read regions except for a region corresponding to an ROI in image data from the memory 15 and output the regions. Note that this processing may be executed by the DSP 14 in the first embodiment.

Since the image sensor 10 can execute the fabrication processing at the selector 16 as described above, it is possible to reduce a processing load on the DSP 14 when the fabrication processing is unnecessary. In addition, since the image sensor 10 can output an image fabricated at the selector 16 without storing the image in the memory 15, it is possible to reduce the used volume of the memory 15, thereby achieving cost and size reduction of the memory 15. As a result, the size of the entire image sensor 10 can be reduced.

4. Third Embodiment

4-1. Description of Imaging Device According to Third Embodiment

The image sensor 10 can increase the processing speed by reading small-volume image data before reading the entire image data from the imager 11 and by detecting a face position. Thus, a third embodiment describes an example in which the processing speed is increased.

Figure 7:
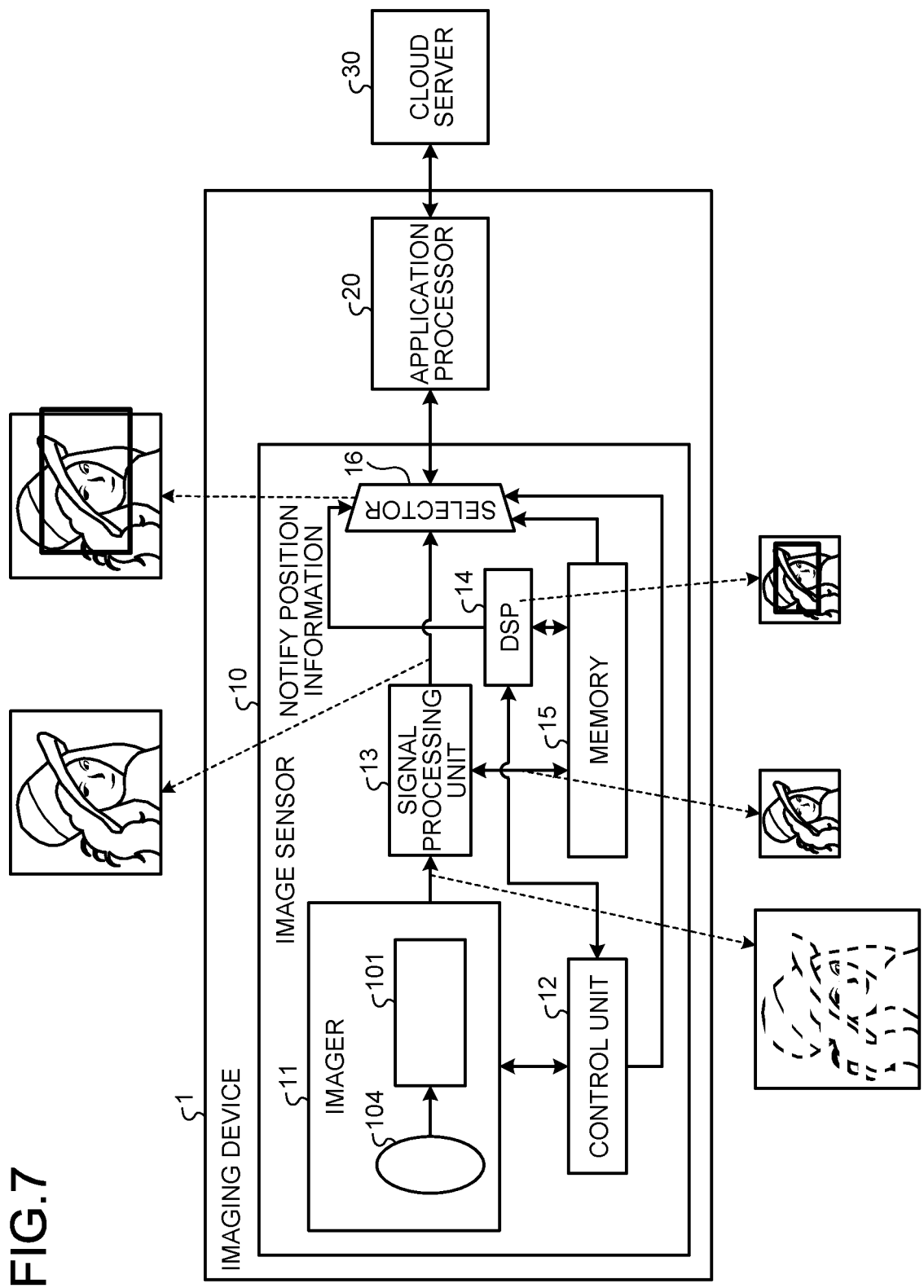
FIG. 7 is a diagram for description of the imaging device according to a third embodiment.

FIG. 7 is a diagram for description of an imaging device according to the third embodiment. As illustrated in FIG. 7, the configuration of the image sensor 10 according to the third embodiment is same as that of the image sensor 10 according to the first embodiment, and thus detailed description thereof is omitted. Difference from the first embodiment will be described below.

For example, as illustrated in FIG. 7, when reading image data from all unit pixels, the imager 11 performs reading from not all unit pixels but thinned target unit pixels and stores thinned small-volume image data in the memory 15. Simultaneously, the imager 11 executes normal reading of image data.

Then, the DSP 14 reads the small-volume image data from the memory 15 and detects a face position from the image data by executing face detection using a learning-completed learning model (Processing 1). Then, the DSP 14 notifies the selector 16 of position information such as an address that specifies the face position.

Thereafter, when having received the normal image data read by the imager 11, the selector 16 specifies a region of interest (ROI) as a fabrication target from the normal image data by using the position information acquired from the DSP 14. Then, the selector 16 generates fabricated image data by executing the fabrication processing such as masking in a region corresponding to the ROI (Processing 2) and outputs the fabricated image data to the application processor 20.

4-2. Process of Processing According to Third Embodiment

Figure 8:
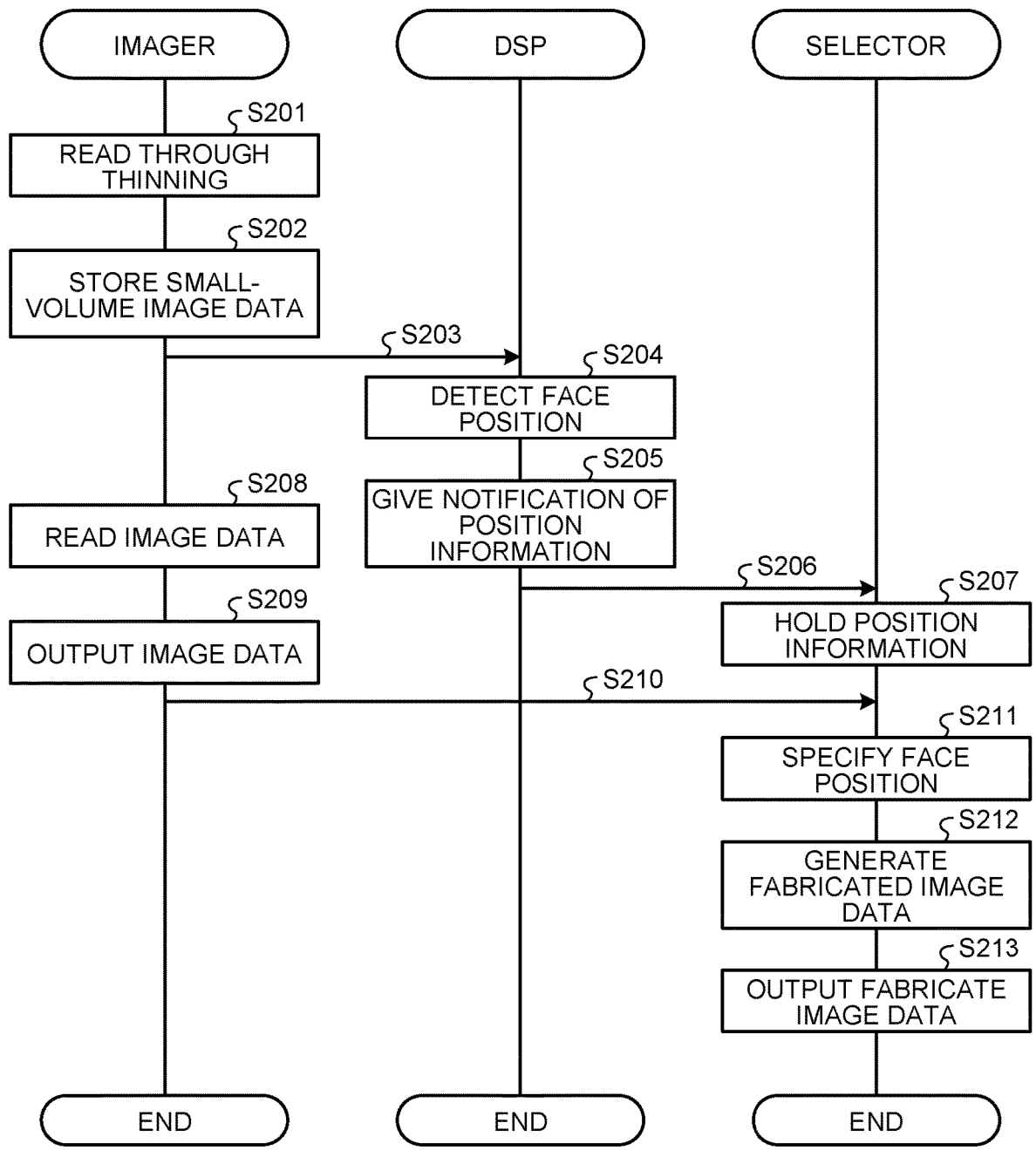
FIG. 8 is a sequence diagram illustrating the process of fabrication processing according to the third embodiment.

The following describes the process of the processing described with reference to FIG. 7. FIG. 8 is a sequence diagram illustrating the process of the fabrication processing according to the third embodiment. As illustrated in FIG. 8, the imager 11 reads an image through thinning (S201) and stores thinned small-volume image data in the memory 15 (S202). Thereafter, the imager 11 reads normal image data.

Simultaneously, the DSP 14 detects a face position by executing face detection on the small-volume image data by using a DNN or the like (S203). Then, the DSP 14 notifies the selector 16 of position information of the detected face position (S205 and S206).

Then, the selector 16 holds the position information of the face position, notification of which is given by the DSP 14 (S207). Thereafter, when the reading of the normal image data is completed, the imager 11 outputs the normal image data to the selector 16 (S209 and S210), and the selector 16 specifies a face position from the normal image data by using the position information of the face position (S211).

Thereafter, the selector 16 generates fabricated image data by fabricating the face position (S212) and outputs the fabricated image data to an external device (S213). For example, the selector 16 clips and outputs only the face position detected by the DNN. In this manner, the image sensor 10 can detect the face position before the reading of the normal image data is completed, and thus can execute the fabrication processing without delay after the image data reading, and the processing speed can be increased as compared to the first embodiment.

5. Chip Configuration of Image Sensor

The following describes an exemplary chip configuration of the image sensor 10 illustrated in FIG. 1 below in detail with reference to the accompanying drawings.

Figure 9:
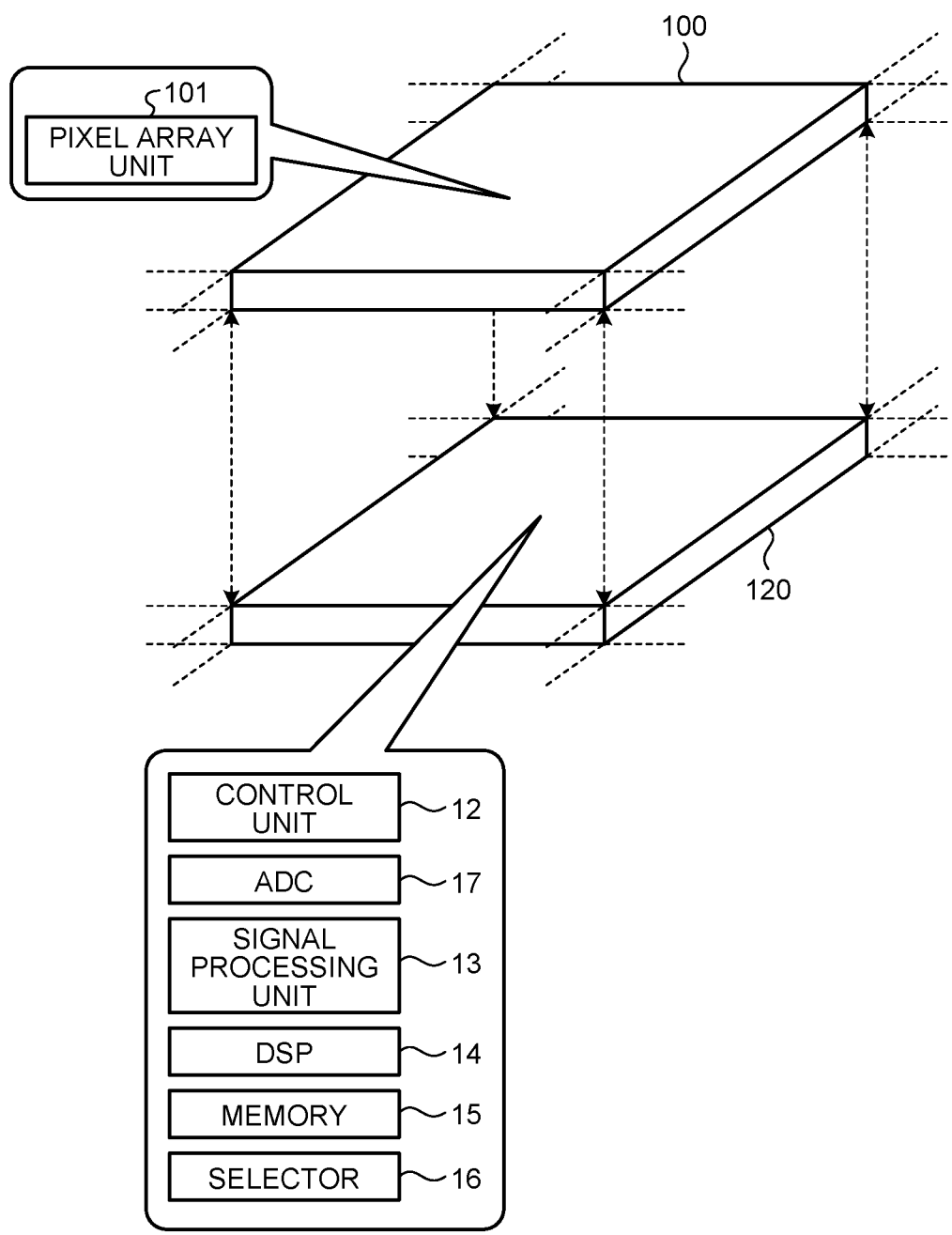
FIG. 9 is a schematic diagram illustrating an exemplary chip configuration of an image sensor according to the present embodiment.

FIG. 9 is a schematic diagram illustrating an exemplary chip configuration of the image sensor according to the present embodiment. As illustrated in FIG. 9, the image sensor 10 has a laminated structure in which a first substrate (die) 100 of a rectangular flat plate shape and a second substrate (die) 120 of a rectangular flat plate shape are bonded to each other.

For example, the first substrate 100 and the second substrate may have the same size. The first substrate 100 and the second substrate 120 may be each a semiconductor substrate such as a silicon substrate.

The pixel array unit 101 of the imager 11 in the configuration of the image sensor 10 illustrated in FIG. 1 is disposed on the first substrate 100. In addition, part or all of the optical system 104 may be provided on the first substrate 100 in an on-chip manner.

The ADC 17, the control unit 12, the signal processing unit 13, the DSP 14, the memory 15, and the selector 16 in the configuration of the image sensor 10 illustrated in FIG. 1 are disposed on the second substrate 120. Note that an interface circuit and a driver circuit (not illustrated) may be disposed on the second substrate 120.

The bonding of the first substrate 100 and the second substrate 120 may be achieved by what is called a chip-on-chip (CoC) scheme in which the first substrate 100 and the second substrate 120 are each divided into a chip, and then, the divided first substrate 100 and second substrate 120 are bonded to each other, by what is called a chip-on-wafer (CoW) scheme in which one (for example, the first substrate 100) of the first substrate 100 and the second substrate 120 is divided into a chip, and then, the divided first substrate 100 is bonded to the second substrate 120 yet to be divided (in other words, as a wafer), or by what is called a wafer-on-wafer (WoW) scheme in which the first substrate 100 and the second substrate 120 as wafers are bonded to each other.

The first substrate 100 and the second substrate 120 may be joined together by, for example, plasma joining. However, the present disclosure is not limited thereto, but various kinds of joining methods may be used.

6. Exemplary Arrangement

Figure 10:
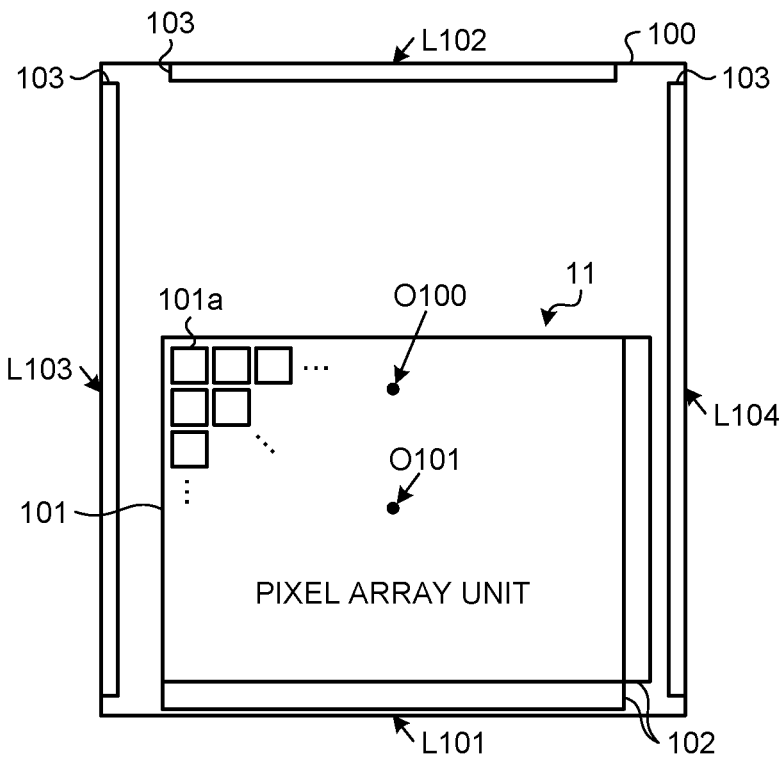
FIG. 10 is a diagram for description of an exemplary arrangement according to the present embodiment.
Figure 11:
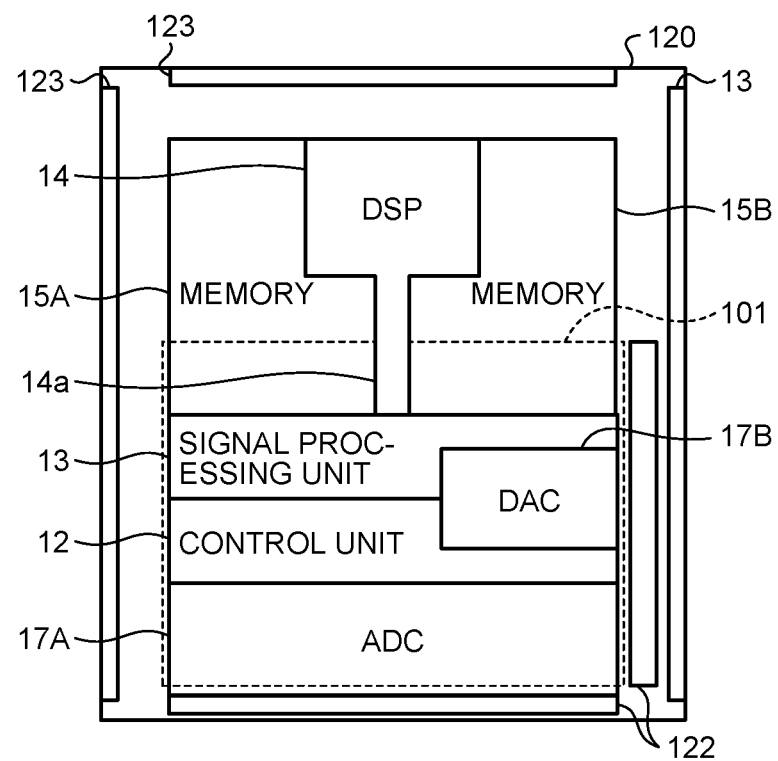
FIG. 11 is a diagram for description of the exemplary arrangement according to the present embodiment.

FIGS. 10 and 11 are each a diagram for description of exemplary arrangement according to the present embodiment. Note that FIG. 10 illustrates exemplary arrangement of the first substrate 100, and FIG. 11 illustrates exemplary arrangement of the second substrate 120.

6-1. Exemplary Arrangement of First Substrate

As illustrated in FIG. 10, the pixel array unit 101 of the imager 11 in the configuration of the image sensor 10 illustrated in FIG. 1 is disposed on the first substrate 100. Note that when part or all of the optical system 104 is mounted on the first substrate 100, the optical system 104 is provided at a position corresponding to the pixel array unit 101.

The pixel array unit 101 is disposed closer to one side L101 among four sides L101 to L104 of the first substrate 100. In other words, the pixel array unit 101 is disposed so that a central part 0101 thereof is closer to the side L101 than a central part 0100 of the first substrate 100. Note that when a surface of the first substrate 100 on which the pixel array unit 101 is provided is rectangular, the side L101 may be, for example, a shorter side. However, the present disclosure is not limited thereto, and the pixel array unit 101 may be disposed closer to a longer side.

A TSV array 102 in which a plurality of penetration wires (through-silicon via; hereinafter referred to as TSV) penetrating through the first substrate 100 are arrayed as wires for electrically connecting each unit pixel 101a in the pixel array unit 101 with the ADC 17 disposed on the second substrate 120 is provided in a region close to the side L101 among the four sides of the pixel array unit 101, in other words, a region between the side L101 and the pixel array unit 101. In this manner, when the TSV array 102 is provided close to the side L101 to which the pixel array unit 101 is close, it is easy to ensure a disposition space for each component such as the ADC 17 on the second substrate 120.

Note that another TSV array 102 may be provided in a region close to the side L104 (or the side L103) among the two sides L103 and L104 intersecting the side L101, in other words, a region between the side L104 (or the side L103) and the pixel array unit 101.

A pad array 103 in which a plurality of pads are arrayed straight is provided to each of the sides L102 and L103 to which the pixel array unit 101 is not disposed close among the four sides L101 to L104 of the first substrate 100. The pads included in the pad array 103 are, for example, a pad (also referred to as a power source pin) to which power voltage for analog circuits such as the pixel array unit 101 and the ADC 17 is applied, a pad (also referred to as a power source pin) to which power voltage for digital circuits such as the signal processing unit 13, the DSP 14, the memory 15, the selector 16, and the control unit 12 is applied, a pad (also referred to as a signal pin) for interfaces such as a mobile industry processor interface (MIPI) and a serial peripheral interface (SPI), and a pad (also referred to as a signal pin) for clock and data inputting and outputting. Each pad is electrically connected with, for example, an external power circuit or interface circuit through a wire. It is preferable that the pad array 103 and the TSV array 102 are sufficiently separated from each other so that influence of signal reflection from a wire connected with each pad in the pad array 103 is negligible.

6-2. Exemplary Arrangement of Second Substrate

As illustrated in FIG. 11, the ADC 17, the control unit 12, the signal processing unit 13, the DSP 14, and the memory 15 in the configuration of the image sensor 10 illustrated in FIG. 1, are disposed on the second substrate 120. Note that in first exemplary arrangement, the memory is divided into two regions of a memory 15A and a memory 15B. Similarly, the ADC 17 is divided into two regions of an ADC 17A and a digital-to-analog converter (DAC) 17B. The DAC 17B is configured to supply reference voltage for AD conversion to the ADC 17A and included as part of the ADC 17 in a broad sense. Although not illustrated in FIG. 10, the selector 16 is disposed on the second substrate 120.

In addition, a wire 122 contacting and electrically connected with each TSV in the TSV array 102 (hereinafter simply referred to as the TSV array 102), which penetrates through the first substrate 100, and a pad array 123 in which a plurality of pads electrically connected with the respective pads in the pad array 103 of the first substrate 100 are arrayed straight are provided on the second substrate 120.

The TSV array 102 and the wire 122 may be connected with each other by, for example, what is called a twin TSV scheme in which the two TSVs of a TSV provided to the first substrate 100 and a TSV provided from the first substrate 100 to the second substrate 120 are connected on the outer surface of a chip, or what is called a shared TSV scheme in which the connection is achieved through a common TSV provided from the first substrate 100 to the second substrate 120. However, the present disclosure is not limited to these schemes, and may employ various kinds of connection forms such as what is called a Cu-Cu bonding scheme of joining copper (Cu) exposed on a joining surface of the first substrate 100 and copper (Cu) exposed on a joining surface of the second substrate 120.

The form of connection between pads in the pad array 103 of the first substrate 100 and the pad array 123 of the second substrate 120 is, for example, wire bonding. However, the present disclosure is not limited thereto and may employ, for example, a through-hole or castellation connection form.

In the exemplary arrangement of the second substrate 120, for example, when the vicinity of the wire 122 connected with the TSV array 102 is defined to be an upstream side, the ADC 17A, the signal processing unit 13, and the DSP 14 are disposed sequentially from the upstream side along flow of a signal read from the pixel array unit 101. Specifically, the ADC 17A, to which a pixel signal read from the pixel array unit 101 is input first, is disposed close to the wire 122 on the most upstream side, the signal processing unit 13 is subsequently disposed, and the DSP 14 is disposed in a region farthest from the wire 122. With this arrangement in which the ADC 17 to the DSP 14 are disposed along signal flow from the upstream side, wires connecting the components can be shortened. Accordingly, it is possible to achieve signal delay reduction, signal propagation loss reduction, S/N ratio improvement, and electric power consumption reduction.

For example, the control unit 12 is disposed close to the wire 122 on upstream side. In FIG. 10, the control unit 12 is disposed between the ADC 17A and the signal processing unit 13. With such an arrangement, it is possible to reduce signal delay, reduce a signal propagation loss, improve the S/N ratio, and reduce electric power consumption when the control unit 12 controls the pixel array unit 101. In addition, there are an advantage in that signal pins and power source pins for analog circuits can be collectively disposed close to the analog circuits (for example, the lower side in FIG. 10), and signal pins and power source pins for the remaining digital circuits can be collectively disposed close to digital circuits (for example, the upper side in FIG. 10), and an advantage in that power source pins for analog circuits and power source pins for digital circuits can be sufficiently separately disposed.

In the arrangement illustrated in FIG. 10, the DSP 14 is disposed on a side opposite to the ADC 17A on the most downstream side. With such an arrangement, in other words, the DSP 14 can be disposed in a region not overlapping with the pixel array unit 101 in a stacking direction (hereinafter simply referred to as an up-down direction) of the first substrate 100 and the second substrate 120.

With this configuration in which the pixel array unit 101 and the DSP 14 do not overlap with each other in the up-down direction, it is possible to reduce the amount of noise generated when the DSP 14 executes signal processing and entering the pixel array unit 101. As a result, when the DSP 14 is operated as a processing unit configured to execute calculation based on a learning-completed model, it is possible to reduce the amount of noise generated due to signal processing by the DSP 14 and entering the pixel array unit 101, and thus it is possible to acquire an image with reduced quality degradation.

Note that the DSP 14 and the signal processing unit 13 are connected with each other through a connection unit 14*a* constituted by part of the DSP 14 or a signal line. The selector 16 is disposed, for example, close to the DSP 14. When the connection unit 14*a* is part of the DSP 14, the DSP 14 partially overlaps with the pixel array unit 101 in the up-down direction, but in such a case as well, it is possible to reduce the amount of noise entering the pixel array unit 101 as compared to a case in which the DSP 14 entirely overlaps with the pixel array unit 101 in the up-down direction.

For example, the memories 15A and 15B are disposed to surround the DSP 14 in three directions. In this manner, when the memories 15A and 15B are disposed to surround the DSP 14, it is possible to average the wiring distance between each memory element on the memory 15 and the DSP 14 and shorten the total distance. Accordingly, it is possible to reduce signal delay, a signal propagation loss, and electric power consumption when the DSP 14 accesses the memory 15.

For example, the pad array 123 is disposed at a position on the second substrate 120, which corresponds to the pad array 103 of the first substrate 100 in the up-down direction. Among the pads included in the pad array 123, pads positioned close to the ADC 17A are used for propagation of power voltage and analog signals for analog circuits (mainly, the ADC 17A). Pads positioned close to the control unit 12, the signal processing unit 13, the DSP 14, and the memories 15A and 15B are used for propagation of power voltage and digital signals for digital circuits (mainly, the control unit 12, the signal processing unit 13, the DSP 14, and the memories 15A and 15B). With such pad arrangement, it is possible to shorten the distance on a wire connecting each pad and each component. Accordingly, it is possible to reduce signal delay, reduce propagation losses of signals and power voltage, improve the S/N ratio, and reduce electric power consumption.

7. Other Embodiments

The above-described processing according to the embodiments may be performed in various kinds of different forms other than the above-described embodiments.

For example, the fabrication processing may execute various kinds of processing in accordance with contents learned by a learning model other than the processing described in the above-described embodiments. For example, it is possible to not only extract the entire face, but also extract the outline of the face, extract only a part such as an eye or nose, extract the owner of the imaging device 1 or a particular person, or extract a part such as a nameplate or a window from an image of a house. In addition, it is possible to extract an outdoor part photographed in indoor image data, distinguish and extract a human and an animal, or extract a part corresponding to a window from image data. Examples of the fabrication processing include processing of reading only an extracted specific region such as a face, not reading only a specific region, coloring a specific region in black, and reading an image obtained by clipping a specific region. Extraction is not limited to a rectangular region but may be performed on an optional region such as a triangular region. The fabrication processing such as masking processing and mosaic processing is not limited to one piece of processing but may be a combination of a plurality of pieces of processing. Extraction of a face position or the like is not limited to the DSP 14 but may be executed by the signal processing unit 13.

Although the above embodiments describe an example of a learning model learned through a DNN, various neural networks such as a recurrent neural network (RNN) and a convolutional neural network (CNN) may be used other than a DNN. The present disclosure is not limited to a learning model using a DNN or the like, but learning models learned by other various kinds of machine learning of a decision tree, a support vector machine, and the like may be used.

Information including processing procedures, control procedures, specific names, and various kinds of data and parameters described in the above specification and drawings may be optionally changed unless otherwise stated. In addition, specific examples, distribution, numerical values, and the like described in the embodiments are merely exemplary and may be optionally changed.

Components of devices illustrated in the drawings represent conceptual functions and are not necessarily physically configured as illustrated in the drawings. In other words, specific forms of dispersion and integration of the devices are not limited to the illustrated forms, and all or some of the devices may be functionally or physically dispersed and integrated in optional units in accordance with various loads and use situations. For example, the control unit 12 and the signal processing unit 13 illustrated in FIG. 1 may be integrated.

8. Exemplary Application to Moving Object

The technology (present technology) of the present disclosure is applicable to various products. For example, the technology of the present disclosure may be achieved as a device mounted on any kind of a moving object such as an automobile, an electric vehicle, a hybrid electric vehicle, an automatic two-wheel vehicle, a bicycle, a personal mobility, an airplane, a drone, a ship, or a robot.

Figure 12:
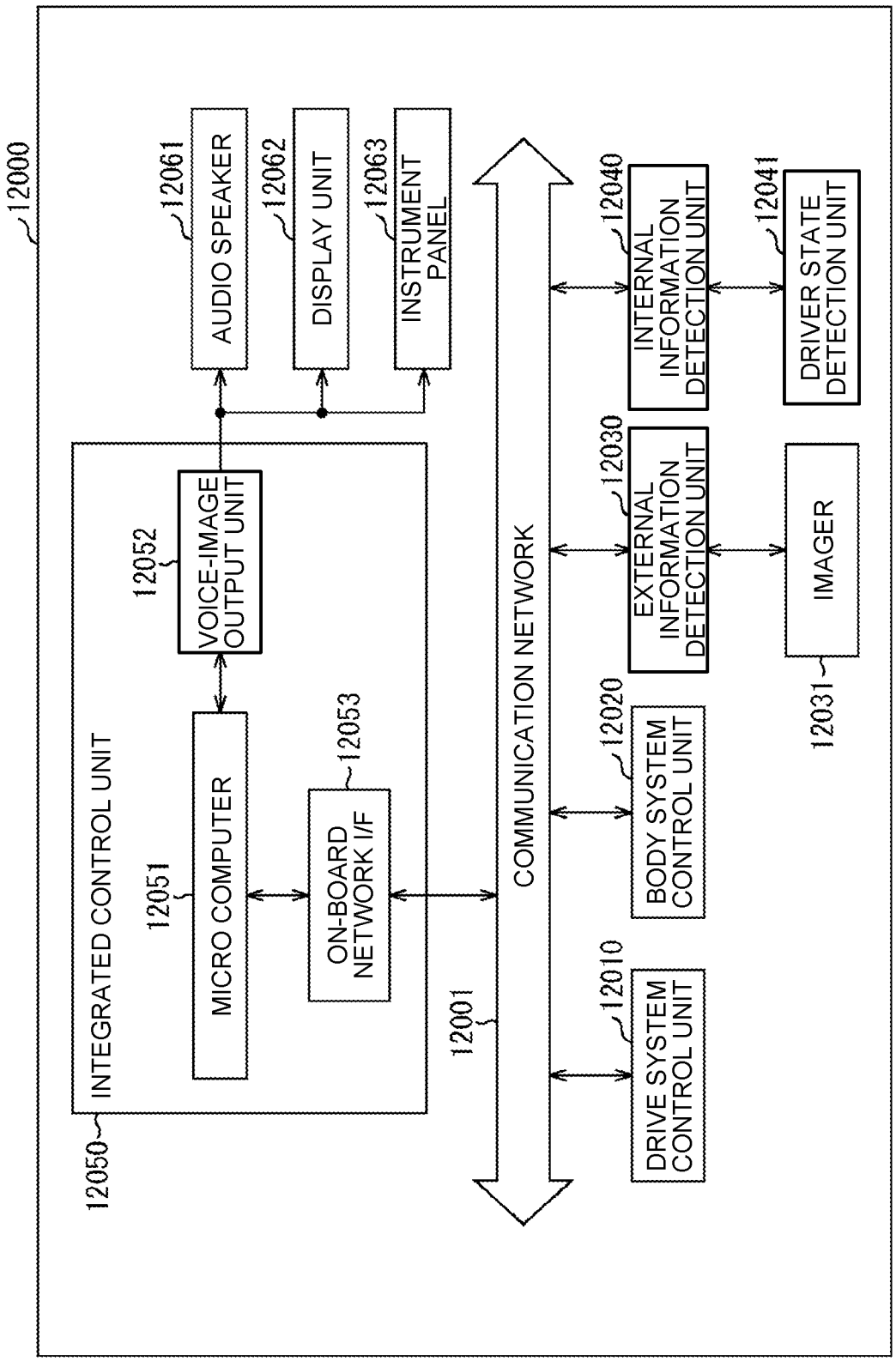
FIG. 12 is a block diagram illustrating an exemplary schematic configuration of a vehicle control system.

FIG. 12 is a block diagram illustrating an exemplary schematic configuration of a vehicle control system as an exemplary moving object control system to which the technology of the present disclosure is applicable.

This vehicle control system 12000 includes a plurality of electronic control units connected with each other through a communication network 12001. In the example illustrated in FIG. 12, the vehicle control system 12000 includes a drive system control unit 12010, a body system control unit 12020, an external information detection unit 12030, an internal information detection unit 12040, and an integrated control unit 12050. In addition, a microcomputer 12051, a voice-image output unit 12052, and an on-board network I/F (interface) 12053 are illustrated as a functional configuration of the integrated control unit 12050.

The drive system control unit 12010 controls operation of devices related to a drive system of a vehicle in accordance with various computer programs. For example, the drive system control unit 12010 functions as a control device for a drive power generation device, such as an internal combustion engine or a drive motor, for generating drive power of the vehicle, a drive power transmission mechanism for transferring the drive power to wheels, a steering mechanism configured to adjust the rudder angle of the vehicle, a braking device configured to generate braking force of the vehicle, and the like.

The body system control unit 12020 controls operation of various devices installed on a vehicle body in accordance with various computer programs. For example, the body system control unit 12020 functions as a control device for a keyless entry system, a smart key system, a power window device, and various lamps such as a head lamp, a rear lamp, a brake lamp, an indicator, and a fog lamp. In this case, the body system control unit 12020 can receive radio wave transmitted from a portable device serving as a key, or various switch signals. The body system control unit 12020 receives inputting of the radio wave or signals and controls a door lock device, a power window device, a lamp, and the like of the vehicle.

The external information detection unit 12030 detects information on the outside of the vehicle on which the vehicle control system 12000 is mounted. For example, the external information detection unit 12030 is connected with an imager 12031. The external information detection unit 12030 causes the imager 12031 to capture an external image and receives the captured image. The external information detection unit 12030 may perform, based on the received image, object detection processing or distance detection processing for a person, a car, an obstacle, a sign, a character on a road surface, and the like.

The imager 12031 is a light sensor configured to receive light and output an electric signal in accordance with the received-light quantity of the light. The imager 12031 may output the electric signal as an image or may output the electric signal as distance measurement information. Light received by the imager 12031 may be visible light or invisible light such as infrared.

The internal information detection unit 12040 detects internal information. The internal information detection unit 12040 is connected with, for example, a driver state detection unit 12041 configured to detect the state of a driver. The driver state detection unit 12041 includes a camera configured to capture an image of the driver, for example, and the internal information detection unit 12040 may calculate the degree of fatigue or concentration of the driver or determine whether the driver is dozing based on detection information input from the driver state detection unit 12041.

The microcomputer 12051 can calculate a control target value of the drive power generation device, the steering mechanism, or the braking device based on the internal and external information acquired by the external information detection unit 12030 and the internal information detection unit 12040, and can output a control command to the drive system control unit 12010. For example, the microcomputer 12051 can perform cooperative control to achieve functions of an advanced driver assistance system (ADAS) including collision avoidance or impact reduction of the vehicle, follow travel based on inter-vehicular distance, vehicle speed maintaining travel, warning for collision of the vehicle, warning for lane deviation of the vehicle, or the like.

The microcomputer 12051 can perform cooperative control for, for example, automated driving in which the vehicle travels autonomously independent from operation by the driver by controlling the drive power generation device, the steering mechanism, the braking device, and the like based on information on surroundings of the vehicle, which is acquired by the external information detection unit 12030 and the internal information detection unit 12040.

The microcomputer 12051 can output a control command to the body system control unit 12020 based on the external information acquired by the external information detection unit 12030. For example, the microcomputer 12051 can control the head lamp in accordance with the position of a preceding vehicle or oncoming vehicle sensed by the external information detection unit 12030, and can perform cooperative control to achieve dimming such as switching from high beam to low beam.

The voice-image output unit 12052 transmits an output signal of at least one of voice and image to an output device capable of visually or audibly giving notification of information to a person on board the vehicle or the outside. In the example of FIG. 12, an audio speaker 12061, a display unit 12062, and an instrument panel 12063 are exemplarily illustrated as the output device. The display unit 12062 may include, for example, at least one of an on-board display and a head-up display.

Figure 13:
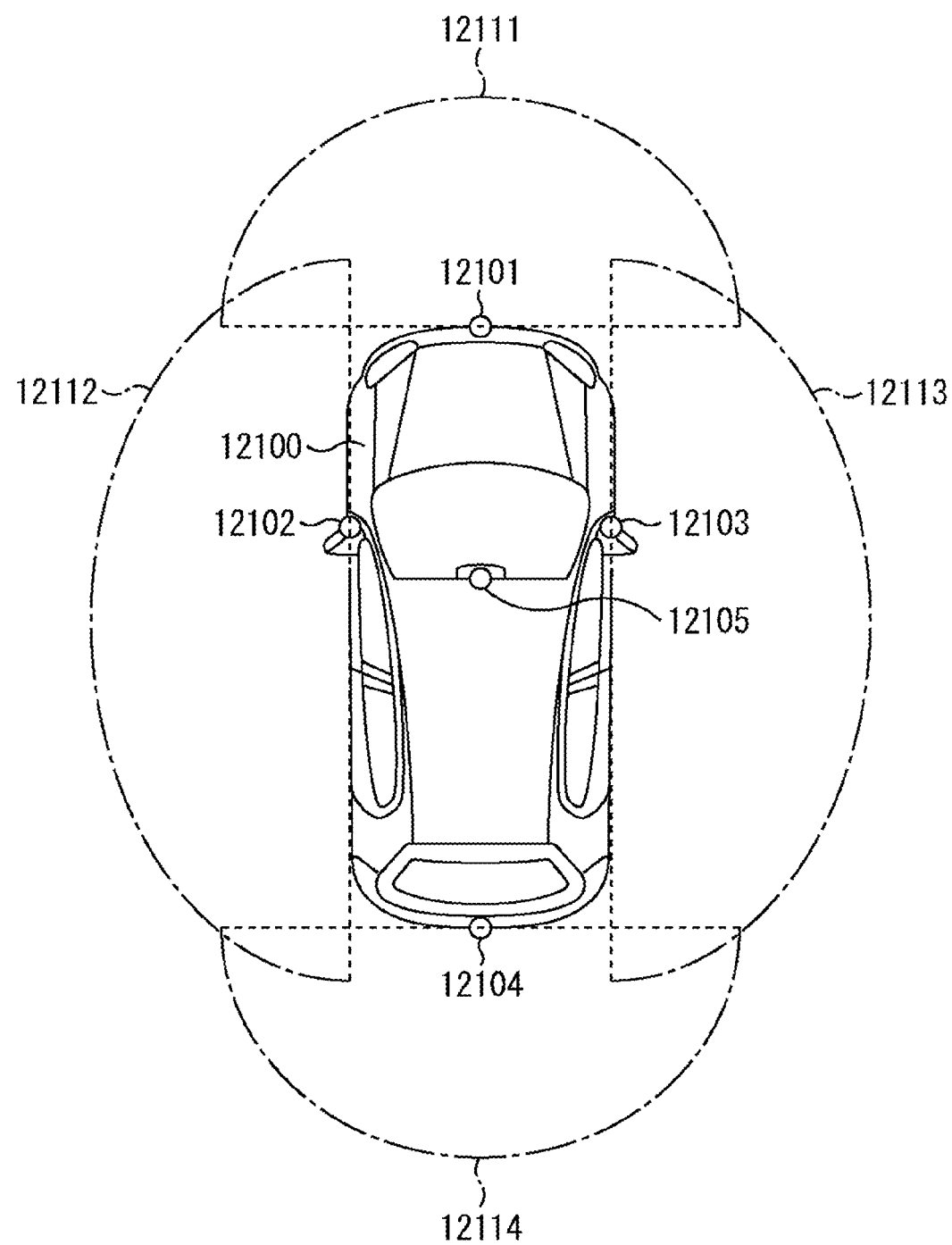
FIG. 13 is an explanatory diagram illustrating exemplary installation positions of an external information detection unit and an imager.

FIG. 13 is a diagram illustrating an exemplary installation position of the imager 12031.

In FIG. 13, imagers 12101, 12102, 12103, 12104, and 12105 are provided as the imager 12031.

The imagers 12101, 12102, 12103, 12104, and 12105 are provided at positions, for example, the front nose, the side mirrors, the rear bumper, and the rear door of a vehicle 12100, an upper part of the front glass in the vehicle, and the like. The imager 12101 provided at the front nose and the imager 12105 provided at the upper part of the front glass in the vehicle mainly acquire images of the front side of the vehicle 12100. The imagers 12102 and 12103 provided at the side mirrors mainly acquire images of the sides of the vehicle 12100. The imager 12104 provided at the rear bumper or the rear door mainly acquires an image of the back side of the vehicle 12100. The imager 12105 provided inside at an upper part of the front glass is mainly used to detect a preceding vehicle, a pedestrian, an obstacle, a traffic light, a traffic sign, a lane, or the like.

Note that FIG. 13 illustrates exemplary image capturing ranges of the imagers 12101 to 12104. An image capturing range 12111 indicates the image capturing range of the imager 12101 provided at the front nose, image capturing ranges 12112 and 12113 indicate the image capturing ranges of the imagers 12102 and 12103 provided at the respective side mirrors, and an image capturing range 12114 indicates the image capturing range of the imager 12104 provided at the rear bumper or the rear door. For example, image data captured by the imagers 12101 to 12104 can be placed together to obtain a panoramic image when the vehicle 12100 is viewed from above.

At least one of the imagers 12101 to 12104 may have a function of acquiring distance information. For example, at least one of the imagers 12101 to 12104 may be a stereo camera made of a plurality of image sensors or may be an image sensor including pixels for phase difference detection.

For example, the microcomputer 12051 calculates the distance to each stereoscopic object in the image capturing ranges 12111 to 12114 and temporal change (speed relative to the vehicle 12100) of the distance based on distance information obtained from the imagers 12101 to 12104, thereby extracting, as a preceding vehicle, in particular, a stereoscopic object that is nearest on the traveling path of the vehicle 12100 and traveling at a predetermined speed (for example, equal to or higher than 0 km/h) in a direction substantially same as that of the vehicle 12100. In addition, the microcomputer 12051 sets an inter-vehicular distance to be ensured to a preceding vehicle in advance, thereby performing automatic brake control (including follow stop control), automatic acceleration control (including follow start control), and the like. In this manner, it is possible to perform cooperative control for, for example, automated driving in which the vehicle travels autonomously independent from operation by the driver.

For example, the microcomputer 12051 can classify, based on distance information obtained from the imagers 12101 to 12104, stereoscopic object data related to a stereoscopic object into a two-wheel vehicle, a standard-size vehicle, a large-size vehicle, a pedestrian, a utility pole, and other stereoscopic objects, extract the stereoscopic object data, and use the stereoscopic object data for obstacle automatic avoidance. For example, the microcomputer 12051 identifies an obstacle in surroundings of the vehicle 12100 as an obstacle that is visually recognizable by the driver of the vehicle 12100 or an obstacle difficult to be visually recognized. Then, the microcomputer 12051 determines a collision risk indicating a danger degree of collision with each obstacle, and in a situation in which the collision risk is equal to or larger than a set value and collision is likely to happen, the microcomputer 12051 can perform operation support for collision avoidance by outputting an alert to the driver through the audio speaker 12061 and the display unit 12062 or performing forced deceleration and avoidance steering through the drive system control unit 12010.

At least one of the imagers 12101 to 12104 may be an infrared camera configured to detect infrared. For example, the microcomputer 12051 can recognize a pedestrian by determining whether the pedestrian exists in images captured by the imagers 12101 to 12104. This pedestrian recognition is performed through, for example, a procedure of extracting feature points in images captured by the imagers 12101 to 12104 as infrared cameras, and a procedure of determining whether an object is a pedestrian by performing pattern matching processing on a series of feature points indicating the outline of the object. When the microcomputer 12051 determines that a pedestrian exists in the images captured by the imagers 12101 to 12104 and recognizes the pedestrian, the voice-image output unit 12052 controls the display unit 12062 to display the recognized pedestrian in superimposition with a rectangular outline line for enhancement. The voice-image output unit 12052 may control the display unit 12062 to display an icon or the like illustrating the pedestrian at a desired position.

The above description is made on an example of the vehicle control system to which the technology of the present disclosure is applicable. The technology of the present disclosure is applicable to the imager 12031 and the like among the above-described components. When the technology of the present disclosure is applied to the imager 12031 and the like, it is possible to achieve size reduction of the imager 12031 and the like, which facilitates interior and exterior designing of the vehicle 12100. In addition, when the technology of the present disclosure is applied to the imager 12031 and the like, it is possible to acquire a clear image with reduced noise and thus provide a more easily viewable captured image to the driver. Accordingly, fatigue of the driver can be reduced.

9. Exemplary Application to Endoscope Operation System

The technology (present technology) of the present disclosure is applicable to various products. For example, the technology of the present disclosure may be applied to an endoscope operation system.

Figure 14:
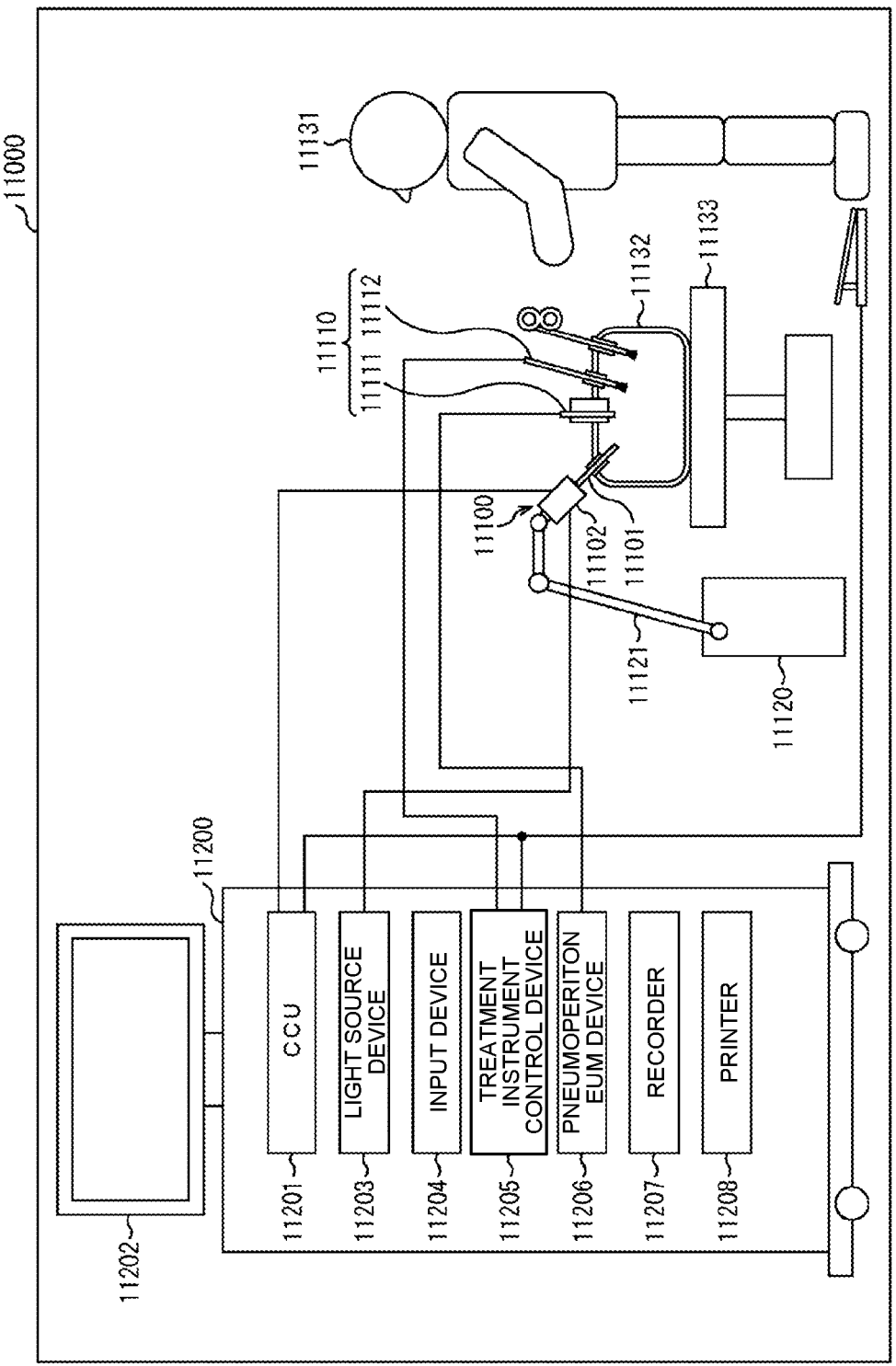
FIG. 14 is a diagram illustrating an exemplary schematic configuration of an endoscope operation system.

FIG. 14 is a diagram illustrating an exemplary schematic configuration of an endoscope operation system to which the technology (present technology) of the present disclosure is applicable.

FIG. 14 illustrates a situation in which an operator (doctor) 11131 performs a medical operation on a patient 11132 on a patient bed 11133 by using this endoscope operation system 11000. As illustrated in FIG. 14, the endoscope operation system 11000 includes an endoscope 11100, other operation instruments 11110 such as a pneumoperitoneum tube 11111 and an energy treatment instrument 11112, a support arm device 11120 supporting the endoscope 11100, and a cart 11200 on which various devices for an endoscopic medical operation are mounted.

The endoscope 11100 includes a lens barrel 11101, a region of which extending from the leading end by a predetermined length is inserted into the body cavity of the patient 11132, and a camera head 11102 connected with the base end of the lens barrel 11101. In the illustrated example, the endoscope 11100 is configured as what is called a rigid scope including the lens barrel 11101 that is rigid, but the endoscope 11100 may be configured as what is called a flexible scope including a flexible lens barrel.

An opening to which an objective lens is fitted is provided at the leading end of the lens barrel 11101. A light source device 11203 is connected with the endoscope 11100, and light generated by the light source device 11203 is guided to the leading end of the lens barrel 11101 by a light guide extending inside the lens barrel 11101 and is emitted toward an observation target in the body cavity of the patient 11132 through the objective lens. Note that the endoscope 11100 may be a direct-view scope, an oblique-view scope, or a side-view scope.

An optical system and an image capturing element are provided inside the camera head 11102, and reflected light (observation light) from the observation target is condensed onto the image capturing element through the optical system. The observation light is photoelectrically converted by the image capturing element, and an electric signal corresponding to the observation light, in other words, an image signal corresponding to an observation image is generated. The image signal is transmitted to a camera control unit (CCU) 11201 as RAW data.

The CCU 11201 includes a central processing unit (CPU) and a graphics processing unit (GPU), and collectively controls operation of the endoscope 11100 and a display device 11202. In addition, the CCU 11201 receives the image signal from the camera head 11102 and provides the image signal with various image processing, such as image development processing (demosaic processing), for displaying an image based on the image signal.

The display device 11202 displays, under control of the CCU 11201, an image based on the image signal provided with the image processing by the CCU 11201.

The light source device 11203 includes a light source such as a light emitting diode (LED) and supplies, to the endoscope 11100, irradiation light for image capturing of an operation site or the like.

An input device 11204 is an input interface for the endoscope operation system 11000. A user can input various kinds of information and instructions to the endoscope operation system 11000 through the input device 11204. For example, the user inputs an instruction to change image capturing conditions (such as irradiation light kind, magnification, and focal length) of the endoscope 11100.

A treatment instrument control device 11205 controls drive of the energy treatment instrument 11112 for tissue cauterization, incision, blood vessel sealing, or the like. A pneumoperitoneum device 11206 feeds gas into the body cavity through the pneumoperitoneum tube 11111 so that the body cavity of the patient 11132 is inflated to obtain a visual field of the endoscope 11100 and a work space for an operator. A recorder 11207 is a device capable of recording various kinds of information related to the medical operation. A printer 11208 is a device capable of printing various kinds of information related to the medical operation in various formats of text, image, graph, and the like.

Note that the light source device 11203 that supplies irradiation light for image capturing of an operation site to the endoscope 11100 may be achieved by a white light source configured as, for example, an LED, a laser beam source, or a combination thereof. When the white light source is configured as a combination of RGB laser beam sources, the output intensity and output timing of each color (wavelength) can be highly accurately controlled, and thus the white balance of a captured image can be adjusted at the light source device 11203. In addition, in this case, an image corresponding to each of RGB can be captured in a time divisional manner by irradiating an observation target with laser beams from the respective RGB laser beam sources in a time divisional manner and controlling drive of the image capturing elements of the camera head 11102 in synchronization with the timings of irradiation. With this method, a color image can be obtained without providing color filters to the image capturing elements.

In addition, drive of the light source device 11203 may be controlled so that the intensity of output light is changed in every predetermined time. Drive of the image capturing elements of the camera head 11102 is controlled in synchronization with the timing of the light intensity change to acquire images in a time divisional manner. The images can be synthesized to generate a high dynamic range image without what are called underexposure and overexposure.

The light source device 11203 may be capable of supplying light in a predetermined wavelength band for special light observation. In the special light observation, for example, what is called narrow band light observation (narrow band imaging) is performed in which an image of a predetermined tissue such as a blood vessel on the surface layer of mucous membrane is captured at high contrast through irradiation with light in a band narrower than the band of irradiation light (in other words, white light) in normal observation by using the wavelength dependency of light absorption in a body tissue. Alternatively, in the special light observation, fluorescence observation may be performed in which an image is obtained by using fluorescence generated through irradiation with excitation light. In the fluorescence observation, for example, a body tissue is irradiated with excitation light to observe fluorescence from the body tissue (self-fluorescence observation), or a reagent such as indocyanine green (ICG) is locally injected into a body tissue and the body tissue is irradiated with excitation light corresponding to the fluorescence wavelength of the reagent to obtain a fluorescence image. The light source device 11203 may be capable of supplying the narrow band light and/or excitation light corresponding to such special light observation.

Figure 15:
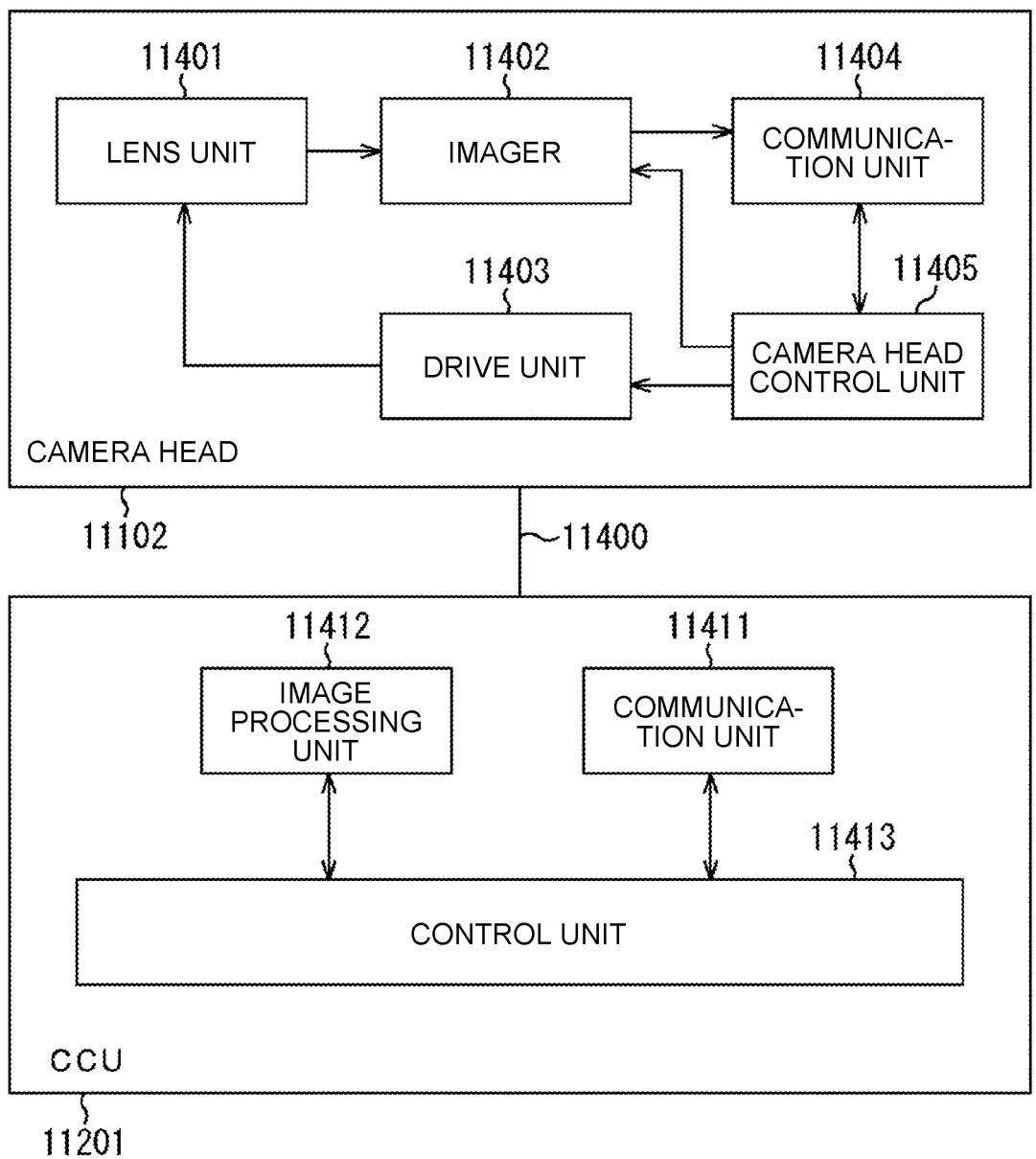
FIG. 15 is a block diagram illustrating exemplary functional configurations of a camera head and a CCU.

FIG. 15 is a block diagram illustrating exemplary functional configurations of the camera head 11102 and the CCU 11201 illustrated in FIG. 14.

The camera head 11102 includes a lens unit 11401, an imager 11402, a drive unit 11403, a communication unit 11404, and a camera head control unit 11405. The CCU 11201 includes a communication unit 11411, an image processing unit 11412, and a control unit 11413. The camera head 11102 and the CCU 11201 are connected with each other through a transmission cable 11400 to perform communication therebetween.

The lens unit 11401 is an optical system provided at a connection part with the lens barrel 11101. The observation light acquired from the leading end of the lens barrel 11101 is guided to the camera head 11102 and incident on the lens unit 11401. The lens unit 11401 is formed by combining a plurality of lenses including a zoom lens and a focus lens.

The imager 11402 may include one image capturing element (what is called a single-plate configuration) or a plurality of image capturing elements (what is called a multiple-plate configuration). When the imager 11402 has the multiple-plate configuration, for example, image signals corresponding to RGB may be generated by the respective image capturing elements and synthesized to obtain a color image. Alternatively, the imager 11402 may include a pair of image capturing elements for acquiring right-eye and left-eye image signals, respectively, for three-dimensional (3D) display. When 3D display is performed, the operator 11131 can more accurately understand the depth of a living body tissue at an operation site. Note that when the imager 11402 has the multiple-plate configuration, a plurality of lens units 11401 are provided for the respective image capturing elements.

The imager 11402 does not necessarily need to be provided to the camera head 11102. For example, the imager 11402 may be provided right after the objective lens inside the lens barrel 11101.

The drive unit 11403 is achieved by an actuator and moves each of the zoom and focus lenses of the lens unit 11401 along the optical axis by a predetermined distance under control of the camera head control unit 11405. Accordingly, the magnification and focal point of an image captured by the imager 11402 can be adjusted as appropriate.

The communication unit 11404 is achieved by a communication device for communicating various kinds of information with the CCU 11201. The communication unit 11404 transmits an image signal acquired from the imager 11402 to the CCU 11201 through the transmission cable 11400 as RAW data.

The communication unit 11404 receives a control signal for controlling drive of the camera head 11102 from the CCU 11201, and supplies the control signal to the camera head control unit 11405. The control signal includes information related to image capturing conditions, such as information on specification of the frame rate of a captured image, information on specification of an exposure value at image capturing, and/or information on specification of the magnification and focal point of the captured image.

Note that the above-described image capturing conditions such as the frame rate, the exposure value, the magnification, and the focal point may be specified by the user as appropriate or may be automatically set by the control unit 11413 of the CCU 11201 based on the acquired image signal. In the latter case, the endoscope 11100 has what are called an auto exposure (AE) function, an auto focus (AF) function, and an auto white balance (AWB) function.

The camera head control unit 11405 controls drive of the camera head 11102 based on the control signal received from the CCU 11201 through the communication unit 11404.

The communication unit 11411 is achieved by a communication device for communicating various kinds of information with the camera head 11102. The communication unit 11411 receives an image signal transmitted from the camera head 11102 through the transmission cable 11400.

The communication unit 11411 transmits a control signal for controlling drive of the camera head 11102 to the camera head 11102. The image signal and the control signal may be transmitted by electrical communication, optical communication, and the like.

The image processing unit 11412 performs various kinds of image processing on an image signal as RAW data transmitted from the camera head 11102.

The control unit 11413 performs various kinds of control related to image capturing of an operation site or the like by the endoscope 11100 and display of a captured image obtained through image capturing of an operation site or the like. For example, the control unit 11413 generates a control signal for controlling drive of the camera head 11102.

In addition, the control unit 11413 causes the display device 11202 to display a captured image of an operation site or the like based on the image signal on which the image processing is performed by the image processing unit 11412. In this case, the control unit 11413 may recognize various objects in the captured image by using various image recognition technologies. For example, the control unit 11413 detects the edge shape, color, and the like of each object included in the captured image to recognize for example, an operation instrument such as forceps, a particular living body site, bleeding, and mist when the energy treatment instrument 11112 is used. When causing the display device 11202 to display the captured image, the control unit 11413 uses a result of the recognition to display various kinds of operation support information on the image of the operation site in a superimposing manner. When the operation support information is displayed in a superimposing manner and presented to the operator 11131, a load on the operator 11131 can be reduced, and the operator 11131 can reliably perform a medical operation.

The transmission cable 11400 connecting the camera head 11102 and the CCU 11201 is an electric signal cable compatible with electric signal communication, an optical fiber compatible with optical communication, or a composite cable thereof.

In the illustrated example, communication is performed in a wired manner by using the transmission cable 11400, but communication between the camera head 11102 and the CCU 11201 may be performed in a wireless manner.

The above description is made on an exemplary endoscope operation system to which the technology of the present disclosure is applicable. The technology of the present disclosure is applicable to, for example, the imager 11402 of the camera head 11102 among the above-described components. When the technology of the present disclosure is applied to the camera head 11102, it is possible to achieve size reduction of the camera head 11102 and the like and thus obtain the endoscope operation system 11000 of a compact size. In addition, when the technology of the present disclosure is applied to the camera head 11102 and the like, it is possible to acquire a clear image with reduced noise, and thus provide a more easily viewable captured image to the operator. Accordingly, fatigue of the operator can be reduced.

Note that the above description is made on an example of an endoscope operation system, but the technology of the present disclosure may be applied to, for example, a microscope operation system.

10. Exemplary Application to Whole Slide Imaging (WSI) System

The technology of the present disclosure is applicable to various products. For example, the technology of the present disclosure may be applied to a pathological diagnosis system with which a doctor or the like diagnoses a lesion by observing cells and tissues collected from a patient, and a support system for the diagnosis (hereinafter referred to as a diagnosis support system). The diagnosis support system may be a whole slide imaging (WSI) system that diagnoses a lesion based on an image acquired by using a digital pathology technology or supports the diagnosis.

Figure 16:
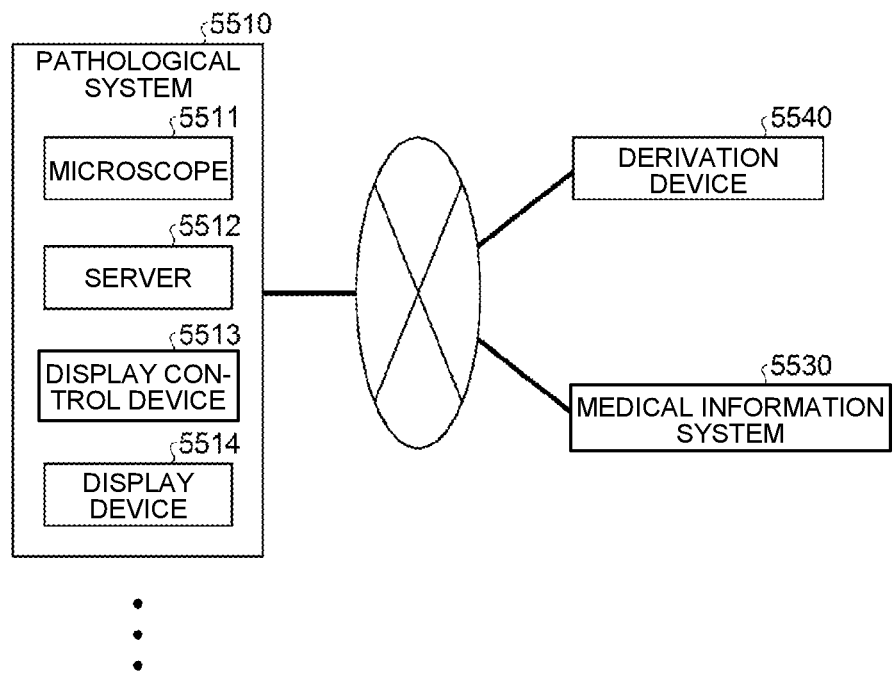
FIG. 16 is a block diagram illustrating an exemplary schematic configuration of a diagnosis support system.

FIG. 16 is a diagram illustrating an exemplary schematic configuration of a diagnosis support system 5500 to which the technology of the present disclosure is applied. As illustrated in FIG. 16, the diagnosis support system 5500 includes one or more pathological systems 5510. The diagnosis support system 5500 may also include a medical information system 5530 and a derivation device 5540.

The one or more pathological systems 5510 are each a system mainly used by a pathologist and installed in, for example, a laboratory or a hospital. The pathological systems 5510 may be installed in hospitals different from each other and each connected with the medical information system 5530 and the derivation device 5540 through various kinds of networks such as a wide area network (WAN) (including the Internet), a local area network (LAN), a public network, and a mobile communication network.

Each pathological system 5510 includes a microscope 5511, a server 5512, a display control device 5513, and a display device 5514.

The microscope 5511 has the function of an optical microscope, performs image capturing of an observation object set in a glass slide, and acquires a pathological image as a digital image. The observation object is, for example, a tissue or a cell collected from a patient or may be a piece of an organ, saliva, or blood.

The server 5512 stores and records the pathological image acquired by the microscope 5511 in a storage unit (not illustrated). When having received a browsing request from the display control device 5513, the server 5512 searches the storage unit (not illustrated) for a pathological image and transfers the searched pathological image to the display control device 5513.

The display control device 5513 transfers a request to browse a pathological image, which is received by a user, to the server 5512. Then, the display control device 5513 displays the pathological image received from the server 5512 on the display device 5514 using a liquid crystal display, an electro-luminescence (EL) display, or a cathode ray tube (CRT) display. Note that the display device 5514 may be compatible with 4K and 8K, and the number of display devices is not limited to one but may be two or more.

When the observation object is a solid matter such as a piece of an organ, the observation object may be, for example, a dyed slice. The slice may be produced by, for example, slicing a block piece cut out from a sample such as an organ. At the slicing, the block piece may be fixed by, for example, paraffin.

The dyeing of the slice may be achieved by various kinds of dyeing, for example, general dyeing to visualize the form of a tissue, such as hematoxylin-eosin (HE) dyeing, or immunity dyeing to visualize the immunity state of a tissue, such as immunohistochemistry (IHC) dyeing. One slice may be dyed by using a plurality of different reagents, or two or more slices (also referred to as adjacent slices) continuously cut out from the same block piece may be dyed by using reagents different from each other.

The microscope 5511 may include a low-resolution imager for image capturing at low resolution, and a high-resolution imager for image capturing at high resolution.

The low-resolution imager and the high-resolution imager may be different optical systems or may be an identical optical system. When the imagers are an identical optical system, the resolution of the microscope 5511 may be changed in accordance with an image capturing target.

The glass slide in which the observation object is set is placed on a stage positioned in the angle of view of the microscope 5511. The microscope 5511 first acquires the entire image in the angle of view by using the low-resolution imager and specifies the region of the observation object from the acquired entire image. Subsequently, the microscope 5511 divides the region in which the observation object exists into a plurality of divided regions of a predetermined size, and sequentially captures images of the divided regions through the high-resolution imager, thereby acquiring a high-resolution image of each divided region. At switching of a target divided region, the stage may be moved, an image capturing optical system may be moved, or both may be moved. Each divided region may overlap with an adjacent divided region to prevent generation of an uncaptured region and the like due to unintended slipping of the glass slide. The entire image may include identification information for associating the entire image with a patient. The identification information may be, for example, a string or a QR code (registered trademark).

High-resolution images acquired by the microscope 5511 are input to the server 5512. The server 5512 divides each high-resolution image into partial images (hereinafter referred to as tile images) of a smaller size. For example, the server 5512 divides one high-resolution image into 100 tile images of 10 tiles×10 tiles in longitudinal and transverse directions. When adjacent divided regions overlap with each other, the server 5512 may provide stitching processing to high-resolution images adjacent to each other by using a technique such as template matching. In this case, the server 5512 may generate tile images by dividing a high-resolution whole image bonded together by the stitching processing. However, the generation of tile images from a high-resolution image may be performed before the above-described stitching processing.

The server 5512 may generate tile images of a smaller size by further dividing each tile image. The generation of such tile images may be repeated until tile images of a size set as a minimum unit are generated.

Once tile images of the minimum unit are generated in this manner, the server 5512 executes, for every tile image, tile synthesis processing of generating one tile image by synthesizing a predetermined number of adjacent tile images. The tile synthesis processing may be repeated until one tile image is finally generated. Through such processing, a tile image group in a pyramid structure including one or more tile images at each level is generated. In this pyramid structure, the number of pixels of tile images of a layer is equal to the number of pixels of tile images of another layer, but the resolutions thereof are different from each other. For example, when four tile images of 2×2 are synthesized to generate one tile image of the upper layer, the resolution of the tile image of the upper layer is half of the resolution of the tile images of the lower layer used in the synthesis.

When such a tile image group in the pyramid structure is established, it is possible to switch the level of detail of the observation object displayed on the display device, depending on a level to which a display target tile image belongs. For example, a narrow region of the observation object may be displayed in detail when tile images of the lowermost layer are used, and a wider region of the observation object may be coarsely displayed as tile images of an upper layer are used.

The generated tile image group in the pyramid structure is stored in the storage unit (not illustrated) together with, for example, identification information (referred to as tile identification information) with which each tile image is uniquely identifiable. When having received, from another device (for example, the display control device 5513 or the derivation device 5540), a request to acquire a tile image including the tile identification information, the server 5512 transmits the tile image corresponding to the tile identification information to the other device.

Note that a tile image as a pathological image may be generated for each image capturing condition such as a focal length or a dye condition. When a tile image is generated for each image capturing condition, a particular pathological image may be displayed side by side with another pathological image corresponding to an image capturing condition different from a particular image capturing condition and corresponding to a region identical to the region of the particular pathological image. The particular image capturing condition may be specified by a browsing person. When a plurality of image capturing conditions are specified by the browsing person, pathological images corresponding to the respective image capturing conditions and an identical region may be displayed side by side.

The server 5512 may store the tile image group in the pyramid structure in another storage device other than the server 5512, for example, in a cloud server. Part or all of the tile image generation processing as described above may be executed at a cloud server or the like.

The display control device 5513 extracts a desired tile image from the tile image group in the pyramid structure in accordance with an input operation from the user and outputs the tile image to the display device 5514. Through such processing, the user can obtain a sense of observing the observation object by changing the magnification of observation. In other words, the display control device 5513 functions as a virtual microscope. The magnification of virtual observation corresponds to resolution in reality.

Note that a high-resolution image may be captured by any method. A high-resolution image may be acquired by capturing images of divided regions while repeating stopping and moving of the stage, or a high-resolution image on a strip may be acquired by capturing images of divided regions while moving the stage at a predetermined speed. The processing of generating tile images from a high-resolution image is not essential, but the resolution of a high-resolution whole image bonded together by the stitching processing may be changed at stages to generate images among which the resolution is different at stages. In this case as well, a low-resolution image of a wide area to a high-resolution image of a narrow area can be presented at stages to the user.

The medical information system 5530 is what is called an electronic medical record system and stores information related to diagnosis, such as information that identifies a patient, disease information of the patient, examination information and image information used for diagnosis, a diagnosis result, and a prescription. For example, a pathological image obtained through image capturing of an observation object of a patient may be temporarily stored through the server 5512 and then displayed on the display device 5514 by the display control device 5513. A pathologist using the pathological system 5510 performs pathological diagnosis based on the pathological image displayed on the display device 5514. A result of the pathological diagnosis performed by the pathologist is stored in the medical information system 5530.

The derivation device 5540 may execute analysis of the pathological image. This analysis can use a learning model produced by machine learning. The derivation device 5540 may derive, as a result of the analysis, a result of classification of a specific region, a result of identification of a tissue, or the like. In addition, the derivation device 5540 may derive identification results such as cell information, numbers, positions, and luminance information, scoring information thereof, and the like. These pieces of information derived by the derivation device 5540 may be displayed as diagnosis support information on the display device 5514 of the pathological system 5510.

Note that the derivation device 5540 may be a server system constituted by one or more servers (including cloud servers). The derivation device 5540 may be incorporated in, for example, the display control device 5513 or the server 5512 in the pathological system 5510. In other words, various kinds of analysis on a pathological image may be executed in the pathological system 5510.

The technology of the present disclosure is excellently applicable to, for example, the microscope 5511 among the above-described components. Specifically, the technology of the present disclosure may be applied to the low-resolution imager and/or the high-resolution imager in the microscope 5511. When the technology of the present disclosure is applied to the low-resolution imager, specification of the region of an observation object in the entire image can be executed in the low-resolution imager. In addition, when the technology of the present disclosure is applied to the high-resolution imager, part or all of the tile image generation processing and the pathological image analysis processing can be executed in the high-resolution imager. Accordingly, part or all of processes from acquisition of a pathological image to analysis of the pathological image can be executed on-the-fly in the microscope 5511, and thus it is possible to output faster and more appropriate diagnosis support information. For example, partial extraction of a specific tissue and partial outputting of an image with consideration on private information can be executed in the microscope 5511, and thus it is possible to achieve reduction of the image capturing time, reduction of the data amount, reduction of the time of a workflow by a pathologist, and the like.

Note that the above-described configuration is not limited to a diagnosis support system but is also applicable to general biological microscopes such as a confocal microscope, a fluorescence microscope, and a video microscope. An observation object may be a living-body specimen such as a culture cell, a fertilized egg, or a sperm, a living-body material such as a cell sheet or a three-dimensional cellular tissue, or a living body such as a zebrafish or a mouse. The observation object is not limited to a glass slide but may be observed in the state of being stored in a well plate, a petri dish, or the like.

A moving image may be generated from still images of the observation object, which is acquired by using a microscope. For example, a moving image may be generated from still images continuously captured for a predetermined duration, and an image sequence may be generated from still images captured at predetermined intervals. When a moving image is generated from still images in this manner, it is possible to analyze, by using machine learning, dynamic characteristics of the observation object, for example, motion such as pulsation, extension, and migration of a cancer cell, a nerve cell, a myocardial tissue, a sperm, or the like, or a division process of a culture cell or a fertilized egg.

The above-described embodiments and modifications may be combined as appropriate without inconsistency of processing contents.

The effects described in the present specification are merely exemplary and not restrictive, but any other effect may be achieved.

Note that the following configuration also belong to the technical scope of the present disclosure.

(1)
A solid-state imaging device comprising:
an imager configured to acquire image data;
a processing unit configured to execute, on the image data or data based on the image data, processing of extracting a specific region based on a neural network calculation model; and
an output unit configured to output image data fabricated based on the specific region or the image data read from the imager based on the specific region.

(2)
The solid-state imaging device according to (1), wherein the processing unit extracts the specific region as a fabrication target from the image data through arithmetic processing using a learning-completed learning model.

(3)
The solid-state imaging device according to (1) or (2), wherein the processing unit generates the fabricated image data by executing masking processing, mosaic processing, or avatar creation processing on the specific region.

(4)
The solid-state imaging device according to claim 1, wherein the processing unit extracts partial image data corresponding to the specific region from the image data.

(5)
The solid-state imaging device according to (4), wherein the output unit outputs the partial image data to outside.

(6)
The solid-state imaging device according to any one of (1) to (5), wherein the output unit outputs partial image data of the specific region extracted by the processing unit to outside as the fabricated image data or the image data read from the imager.

(7)
The solid-state imaging device according to any one of (1) to (5), wherein the output unit outputs image data other than the specific region extracted by the processing unit to outside as the fabricated image data or the image data read from the imager.

(8)
The solid-state imaging device according to any one of (1) to (7), further comprising a control unit configured to control reading of image data from the imager, wherein
the control unit reads partial image data corresponding to the specific region from the imager.

(9)
The solid-state imaging device according to any one of (1) to (7), further comprising a control unit configured to control reading of image data from the imager, wherein the control unit reads image data not including the specific region from the imager.

(10)
The solid-state imaging device according to any one of (1) to (9), wherein the specific region is a region including at least one of the face, eyes, nose, and mouth of a person, a window, and a nameplate.

(11)

The solid-state imaging device according to any one of (1) to (10), wherein
- at reading of a captured image, the imager acquires the image data through thinning of reading target unit pixels, and
- the processing unit extracts the specific region from the thinned image data.

(12)

An electronic device comprising:
- a solid-state imaging device including an imager configured to acquire image data, a processing unit configured to execute, on data based on the image data, processing of extracting a specific region based on a neural network calculation model, and an output unit configured to output image data fabricated based on the specific region or the image data read from the imager based on the specific region; and
- a control device configured to execute processing through an application on the fabricated image data output from the solid-state imaging device or the image data read from the imager.

REFERENCE SIGNS LIST 1 imaging device
10 image sensor
11 imager
12 control unit
13 signal processing unit
14 DSP
15 memory
16 selector
20 application processor
30 cloud server

The invention claimed is:

1. A solid-state imaging device comprising:
an imager configured to sense and capture first image data and output the first image data and thinned image data through thinning of reading target unit pixels in the first image data;
a processor configured to
execute, on the thinned image data, processing of extracting at least one specific region based on a neural network calculation model; and
a selector configured to output, based on a user setting, second image data or to output third image data by determining whether the user setting is a fabrication processing mode or a normal processing mode,
in response to determining the user setting is the fabrication processing mode, generating the second image data using fabrication processing on the thinned image data, and
in response to determining the user setting is the normal processing mode, outputting the first image data as the third image data; wherein
the second image data is fabricated based on at least one of masking processing, mosaic processing, or avatar creation processing on the at least one specific region,
the third image data is read from the imager based on the at least one specific region, and
the imager, the processor, and the selector are arranged in a single chip.

2. The solid-state imaging device according to claim 1, wherein the processor extracts the at least one specific region as a fabrication target from the first image data through arithmetic processing using a learning-completed learning model.

3. The solid-state imaging device according to claim 1, wherein the processor extracts partial image data corresponding to the at least one specific region from the first image data.

4. The solid-state imaging device according to claim 3, wherein the selector outputs the partial image data to outside.

5. The solid-state imaging device according to claim 1, wherein the selector outputs partial image data of the at least one specific region extracted by the processor to outside as the second image data or the third image data read from the imager.

6. The solid-state imaging device according to claim 1, wherein the selector outputs image data other than the at least one specific region extracted by the processor to outside as the second image data or the third image data read from the imager.

7. The solid-state imaging device according to claim 1, further comprising a control unit configured to control reading of the first image data from the imager, wherein
the control unit reads partial image data corresponding to the at least one specific region from the imager.

8. The solid-state imaging device according to claim 1, further comprising a control unit configured to control reading of the first image data from the imager, wherein
the control unit reads image data not including the at least one specific region from the imager.

9. The solid-state imaging device according to claim 1, wherein the at least one specific region is a region including at least one of the face, eyes, nose, and mouth of a person, a window, and a nameplate.

10. An electronic device comprising:
a solid-state imaging device including an imager configured to sense and capture first image data and output the first image data and thinned image data through thinning of reading target unit pixels in the first image data, a processor configured to execute, on the thinned image data, processing of extracting at least one specific region based on a neural network calculation model, and a selector configured to output, based on a user setting, second image data or to output third image data by determining whether the user setting is a fabrication processing mode or a normal processing mode, in response to determining the user setting is the fabrication processing mode, generating the second image data using fabrication processing on the thinned image data, and in response to determining the user setting is the normal processing mode, outputting the first image data as the third image data, wherein
the second image data is fabricated based on at least one of masking processing, mosaic processing, or avatar creation processing on the at least one specific region, and
the third image data is read from the imager based on the at least one specific region; and
a controller configured to execute processing through an application on the first image data output from the solid-state imaging device or the third image data read from the imager; wherein
the solid-state imaging device, the selector, and the controller are arranged in a single chip.

11. The electronic device according to claim 10, wherein the processor extracts the at least one specific region as a fabrication target from the first image data through arithmetic processing using a learning-completed learning model.

12. The electronic device according to claim 10, wherein the at least one specific region is a region including at least one of the face, eyes, nose, and mouth of a person, a window, and a nameplate.

13. The electronic device according to claim 10, wherein
   at reading of a captured image, the imager outputs thinned image data through thinning of reading target unit pixels, and
   the processor extracts the at least one specific region from the thinned image data.

14. The electronic device according to claim 10, wherein the processor extracts partial image data corresponding to the at least one specific region from the first image data.

15. The electronic device according to claim 10, wherein the selector outputs the partial image data to outside.

16. The electronic device according to claim 10, wherein the selector outputs partial image data of the at least one specific region extracted by the processor to outside as the second image data or the third image data read from the imager.

17. The electronic device according to claim 10, wherein the selector outputs image data other than the at least one specific region extracted by the processor to outside as the second image data or the third image data read from the imager.

* * * * *